[19] United States Patent
Ishihara et al.

(10) Patent No.: US 10,653,486 B2
(45) Date of Patent: May 19, 2020

(54) REMOTE CONTROL APPARATUS FOR MEDICAL EQUIPMENT

(71) Applicant: MEDICAROID CORPORATION, Kobe-shi, Hyogo (JP)

(72) Inventors: Kazuki Ishihara, Kobe (JP); Shiro Horita, Kobe (JP)

(73) Assignee: MEDICAROID CORPORATION, Kobe-shi (JP)

( * ) Notice: Subject to any disclaimer, the term of this patent is extended or adjusted under 35 U.S.C. 154(b) by 74 days.

(21) Appl. No.: 16/000,374

(22) Filed: Jun. 5, 2018

(65) Prior Publication Data
US 2018/0353246 A1 Dec. 13, 2018

(30) Foreign Application Priority Data
Jun. 8, 2017 (JP) .................. 2017-113345

(51) Int. Cl.
*A61B 34/00* (2016.01)
*A61B 34/35* (2016.01)
(Continued)

(52) U.S. Cl.
CPC .............. *A61B 34/25* (2016.02); *A61B 34/30* (2016.02); *A61B 34/35* (2016.02); *A61B 34/37* (2016.02); *A61B 34/74* (2016.02); *A61B 90/37* (2016.02); *A61B 90/50* (2016.02); *A61B 34/76* (2016.02); *A61B 2017/00212* (2013.01); *A61B 2090/506* (2016.02); *A61B 2090/508* (2016.02)

(58) Field of Classification Search
CPC .... A61B 2017/00212; A61B 2090/506; A61B 2090/508; A61B 34/25; A61B 34/30; A61B 34/35; A61B 34/37; A61B 34/74; A61B 34/76; A61B 90/37; A61B 90/50; A61B 17/00; A61B 18/00; F16M 11/041; F16M 11/10; F16M 11/18; F16M 11/2021; F16M 11/2064; F16M 11/08; F16M 11/14; F16M 2200/02; F16M 2200/06

See application file for complete search history.

(56) References Cited

U.S. PATENT DOCUMENTS

2003/0220564 A1   11/2003   Wilkins et al.
2008/0001866 A1*   1/2008   Martin .................. F16M 11/10
                                                                345/84
(Continued)

FOREIGN PATENT DOCUMENTS

EP    2907468 A1    8/2015
EP    3184069 A1    6/2017
(Continued)

*Primary Examiner* — Hong Zhou
(74) *Attorney, Agent, or Firm* — Metrolex IP Law Group, PLLC

(57) ABSTRACT

A remote control apparatus according to one or more embodiments includes a manipulator that supports surgical equipment; a display configured to display an image captured by an endoscopy; a display supporting arm that includes a joint and a locking mechanism and supports the display, the locking mechanism is configured to lock the joint; an operation handle that allows an operator to operate the manipulator; and an unlocking mechanism configured, in response to an operation by the operator, to unlock the locked joint of the display supporting arm.

22 Claims, 12 Drawing Sheets

(51) Int. Cl.
*A61B 90/00* (2016.01)
*A61B 90/50* (2016.01)
*A61B 34/30* (2016.01)
*A61B 34/37* (2016.01)
*A61B 17/00* (2006.01)

(56) References Cited

U.S. PATENT DOCUMENTS

| | | | |
|---|---|---|---|
| 2008/0132786 A1* | 6/2008 | Asai | A61B 8/14 |
| | | | 600/437 |
| 2011/0118748 A1 | 5/2011 | Itkowitz | |
| 2012/0182709 A1* | 7/2012 | Asai | A61B 8/4405 |
| | | | 361/810 |
| 2014/0121834 A1* | 5/2014 | Ogawa | B25J 3/04 |
| | | | 700/257 |
| 2014/0192504 A1* | 7/2014 | Richard | F16M 11/10 |
| | | | 361/807 |
| 2014/0353453 A1* | 12/2014 | Quijano | F16M 11/18 |
| | | | 248/419 |
| 2015/0025547 A1 | 1/2015 | Hannaford et al. | |
| 2015/0224643 A1 | 8/2015 | Ernsperger et al. | |
| 2016/0374771 A1 | 12/2016 | Mirbagheri et al. | |
| 2018/0092706 A1* | 4/2018 | Anderson | A61B 34/30 |
| 2018/0289445 A1* | 10/2018 | Krinninger | B25J 13/084 |

FOREIGN PATENT DOCUMENTS

| | | |
|---|---|---|
| JP | 2004-337443 A | 12/2004 |
| JP | 2005-526567 A | 9/2005 |
| JP | 2005-292452 A | 10/2005 |
| JP | 2005-342056 A | 12/2005 |
| JP | 2007-117291 A | 5/2007 |
| JP | 2009-254725 A | 11/2009 |
| JP | 2012-000199 A | 1/2012 |
| JP | 2015-128681 A | 7/2015 |
| WO | 2011/116332 A2 | 9/2011 |
| WO | 2011/116332 A3 | 9/2011 |
| WO | 2016/077552 A1 | 5/2016 |
| WO | 2016/176755 A1 | 11/2016 |
| WO | 2018/067611 A1 | 4/2018 |

* cited by examiner

FIXED STATE

UNLOCK STATE

DETACH STATE

FIXED STATE

UNLOCK STATE

DETACH STATE

FIXED STATE

UNLOCK STATE

DETACH STATE

REMOTE CONTROL APPARATUS FOR MEDICAL EQUIPMENT

CROSS REFERENCE TO RELATED APPLICATIONS

This application claims priority based on 35 USC 119 from prior Japanese Patent Applications No. 2017-113345 filed on Jun. 8, 2017, entitled "REMOTE CONTROL APPARATUS FOR MEDICAL EQUIPMENT", the entire contents of which are incorporated herein by reference.

BACKGROUND

The disclosure relates to a remote control apparatus for medical equipment.

In recent years, surgical robots have been used in various surgeries, and remote control apparatuses for surgical robots are expected to improve in operability. In order to improve the operator's immersive feeling to surgeries, most conventional remote control apparatuses are provided with a viewer that the operator looks into with his/her face affixed thereon, as described in Patent Literature 1.

Patent Literature 1: WO 2016/077552

SUMMARY

In the remote control apparatus of Patent Literature 1, the position of the display is adjustable. However, the position of the display can be adjusted just in a simple manner, by separately controlling the height, depth, and angle thereof. In addition, the adjustable range of the position of the display is limited, so that the position of the display cannot be moved enough for the operator to change his/her posture.

An object of an embodiment is to provide a remote control apparatus for medical equipment, which is able to easily change the position of a display and thereby allows an operator to freely take a desired posture even while viewing the display.

An aspect of the disclosure is a remote control apparatus for a surgery assisting system including a manipulator that supports surgical equipment. The remote control apparatus includes: a display configured to display an image captured by an endoscopy; a display supporting arm that includes a joint and a locking mechanism and supports the display, the locking mechanism is configured to lock the joint; an operation handle that allows an operator to operate the manipulator; and an unlocking mechanism configured, in response to an operation by the operator, to unlock the locked joint of the display supporting arm.

A second aspect of the disclosure is a remote control apparatus for a surgery assisting system including a manipulator that supports surgical equipment. The remote control apparatus according to the second aspect includes: a display that displays an image captured by an endoscope; a display supporting arm that includes joints and locking mechanisms and supports the display, the joints including a first joint rotating around a horizontal axis and a second joint rotating around a horizontal axis, the locking mechanisms being disposed for the respective joints and locking the corresponding joints; an operation handle that allows the operator to operate the manipulator; and an unlocking mechanism configured, in response to an operation by the operator, to unlock the joints of the display supporting arm which are locked by the locking mechanisms. The unlocking mechanism that is being operated by the operator unlocks the joints locked by the locking mechanisms.

According to at least one of the aspects, the operator of the remote control apparatus can freely move the display to a desired position even during a surgery, for example.

DETAILED DESCRIPTION

Embodiments are explained with reference to drawings hereinafter.

First Embodiment

[Configuration of Remote Control Apparatus]

The configuration of a remote control apparatus 100 according to a first embodiment is described with reference to FIGS. 1 to 11.

Figure 1:
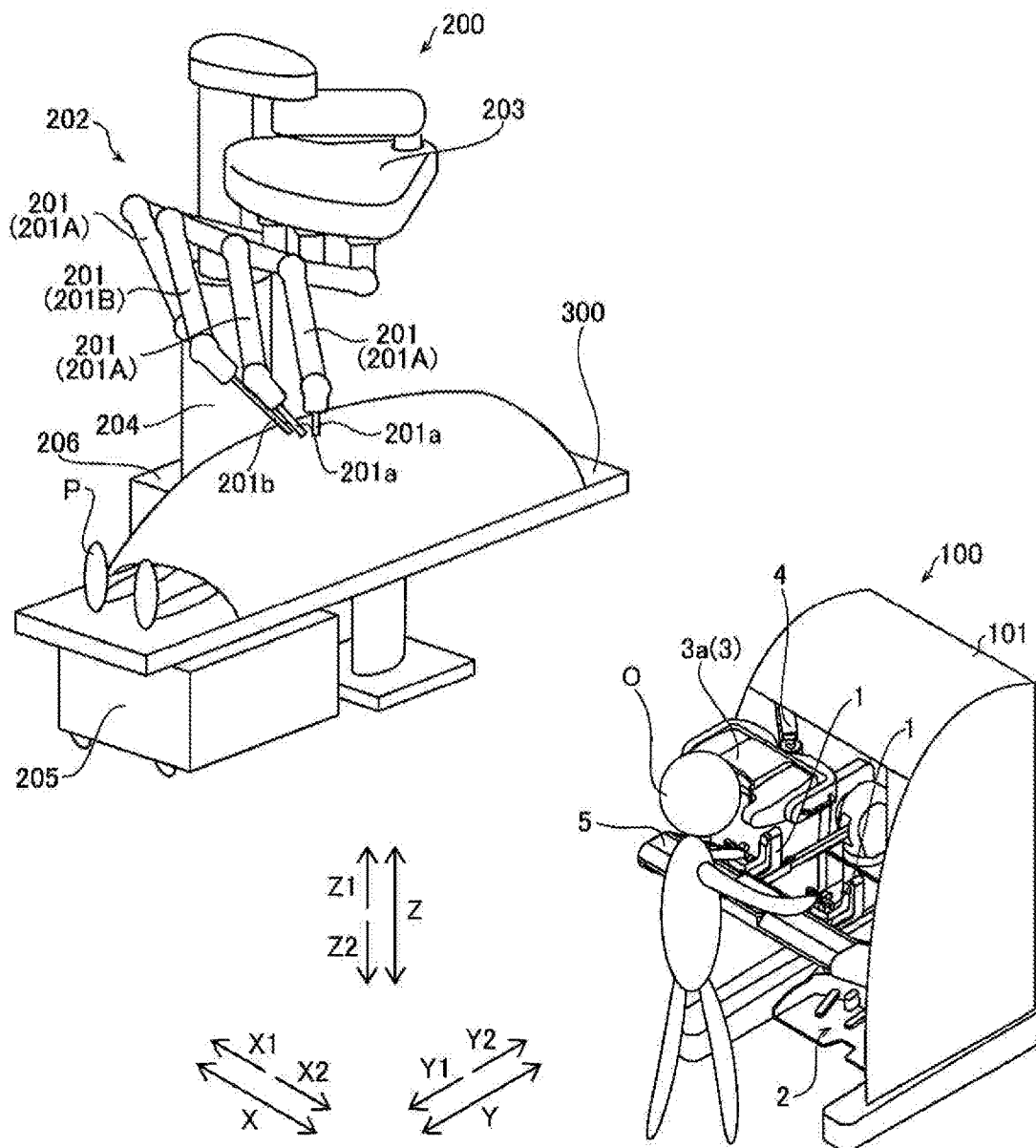
FIG. 1 is a schematic view illustrating a remote control apparatus according to one or more embodiments.

As illustrated in FIG. 1, the remote control apparatus 100 is provided for teleoperation of medical equipment included in a patient-side system 200. When an operator O, as a surgeon, inputs an action mode instruction to be executed by the patient-side system 200, to the remote control apparatus 100, the remote control apparatus 100 transmits the action mode instruction to the patient-side system 200 through a controller 206. In response to the action mode instruction transmitted from the remote control apparatus 100, the patient-side system 200 operates medical equipment, such as surgical instruments and an endoscope, held by surgical manipulators 201. This allows for minimally invasive surgery. A surgery assisting system includes the remote control apparatus 100 and the patient-side system 200 including the surgical manipulators 201. The remote control apparatus 100 is an example of a remote control apparatus for medical equipment.

The patient-side system 200 constitutes an interface to perform a surgery for a patient P. The patient-side system 200 is placed beside an operation table 300 on which the patient P lies. The patient-side system 200 includes plural surgical manipulators 201. One of the surgical manipulators 201 holds an endoscope 201b while the others hold surgical instruments (instruments 201a). The surgical manipulator 201 holding surgical instruments (instruments 201a) function as instrument arms 201A while the surgical manipulator 201 holding the endoscope 201b functions as a camera arm 201B. The instrument arms 201A and camera arm 201B are commonly supported by a platform 203. Each of the surgical manipulators 201 includes plural joints. Each joint includes a driver including a servo-motor and a position detector such as an encoder. The surgical manipulators 201 are configured so that medical equipment attached to each surgical manipulator 201 is controlled by a driving signal given through the controller 206, to perform a desired movement.

The platform 203 is supported by a positioner 202 placed on the floor of an operation room. The positioner 202 includes a column 204 and a base 205. The column 204 includes an elevating shaft adjustable in the vertical direction. The base 205 includes wheels and is movable on the floor surface.

The instrument arms 201A detachably hold the instruments 201a as the medical equipment at the tips thereof. Each instrument 201a includes a housing and an end effector. The housing is attached to the instrument arm 201A. The end effector is provided at the tip of an elongated shaft. The end effector is grasping forceps, a hook, scissors, a high-frequency knife, a snare wire, a clamp, or a stapler, for example. The end effector is not limited to those and can be various types of treatment tools. In surgeries using the patient-side system 200, the instrument arms 201A are introduced into the body of the patient P through a cannula (trocar) placed on the body surface of the patient P, and the end effector of each instrument 201a is located near the surgery site.

To the tip of the camera arm 201B, the endoscope 201b (see FIG. 4), as the medical equipment, is detachably attached. The endoscope 201b captures an image within the body cavity of the patient P. The captured image is outputted to the remote control apparatus 100. The endoscope 201b is a 3D endoscope capable of capturing a three-dimensional image or a 2D endoscope. In surgeries using the patient-side system 200, the camera arm 201B is introduced into the body of the patient P through a trocar placed on the body surface of the patient P, and the endoscope 201b is located near the surgery site. The endoscope 201b is an example of an imaging section, or an imaging device.

The remote control apparatus 100 constitutes the interface with the operator O. The remote control apparatus 100 is an apparatus that allows the operator O to operate medical equipment held by the surgical manipulators 201. Specifically, the remote control apparatus 100 is configured to transmit action mode instructions which are inputted by the operator O and are to be executed by the instruments 201a and endoscope 201b, to the patient-side system 200 through the controller 206. The remote control apparatus 100 is installed beside the operation table 300 so that the operator O can see the state of the patient P very well while operating operation handles 1, for example. The remote control apparatus 100 may be configured to transmit the action mode instructions wirelessly and installed in a room different from the operation room where the operation table 300 is installed.

The action modes to be executed by the instruments 201a include a mode of actions to be taken by each instrument 201a (a series of positions and postures) and actions to be executed by the function of each instrument 201a. For the instrument 201a which is a pair of grasping forceps, for example, the action mode to be executed by the instrument 201a includes roll and pitch positions of the wrist of the end effector and the action to open or close the jaws. For the instrument 201a which is a high-frequency knife, the action mode to be executed by the instrument 201a includes vibration of the high-frequency knife, specifically, supply of current to the high-frequency knife. For the instrument 201a which is a snare wire, the action mode to be executed by the instrument 201a includes a capturing action and an action to release the captured object and moreover includes an action to supply current to a bipolar or monopolar instrument to burn off the surgery site.

The action mode to be executed by the endoscope 201b includes the position and posture of the tip of the endoscope 201b or setting of the zoom magnification, for example.

As illustrated in FIG. 1, the remote control apparatus 100 is provided with a cover 101. The cover 101 covers the right and left sides of the remote control apparatus 100 (on X1 and X2 sides), the back side (on Y2 side), and the top side (on the Z1 side). FIGS. 2 to 11 illustrate the remote control apparatus 100 with the cover 101 removed for convenience.

Figure 2:
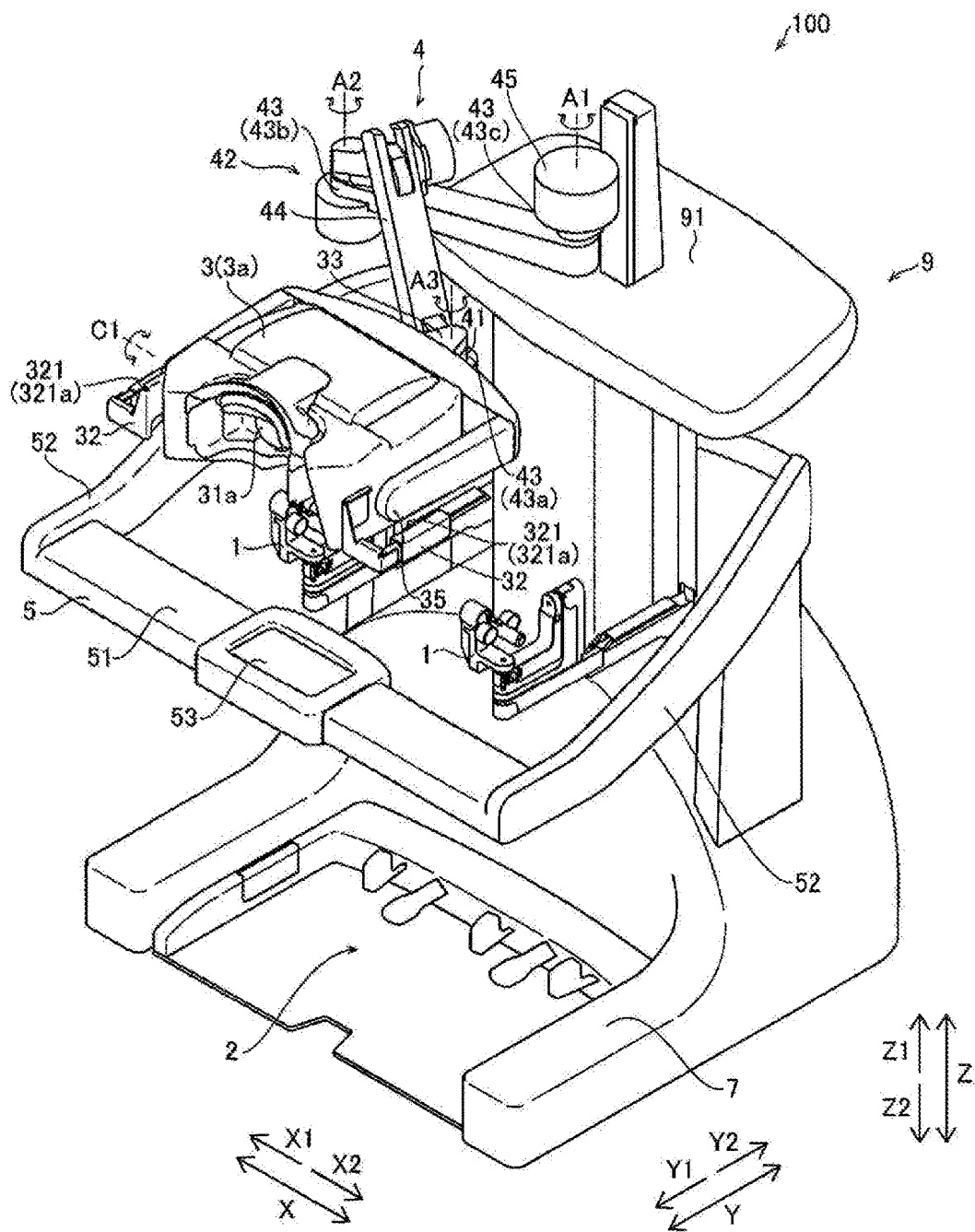
FIG. 2 is a perspective view illustrating the remote control apparatus according to a first embodiment.
Figure 4:
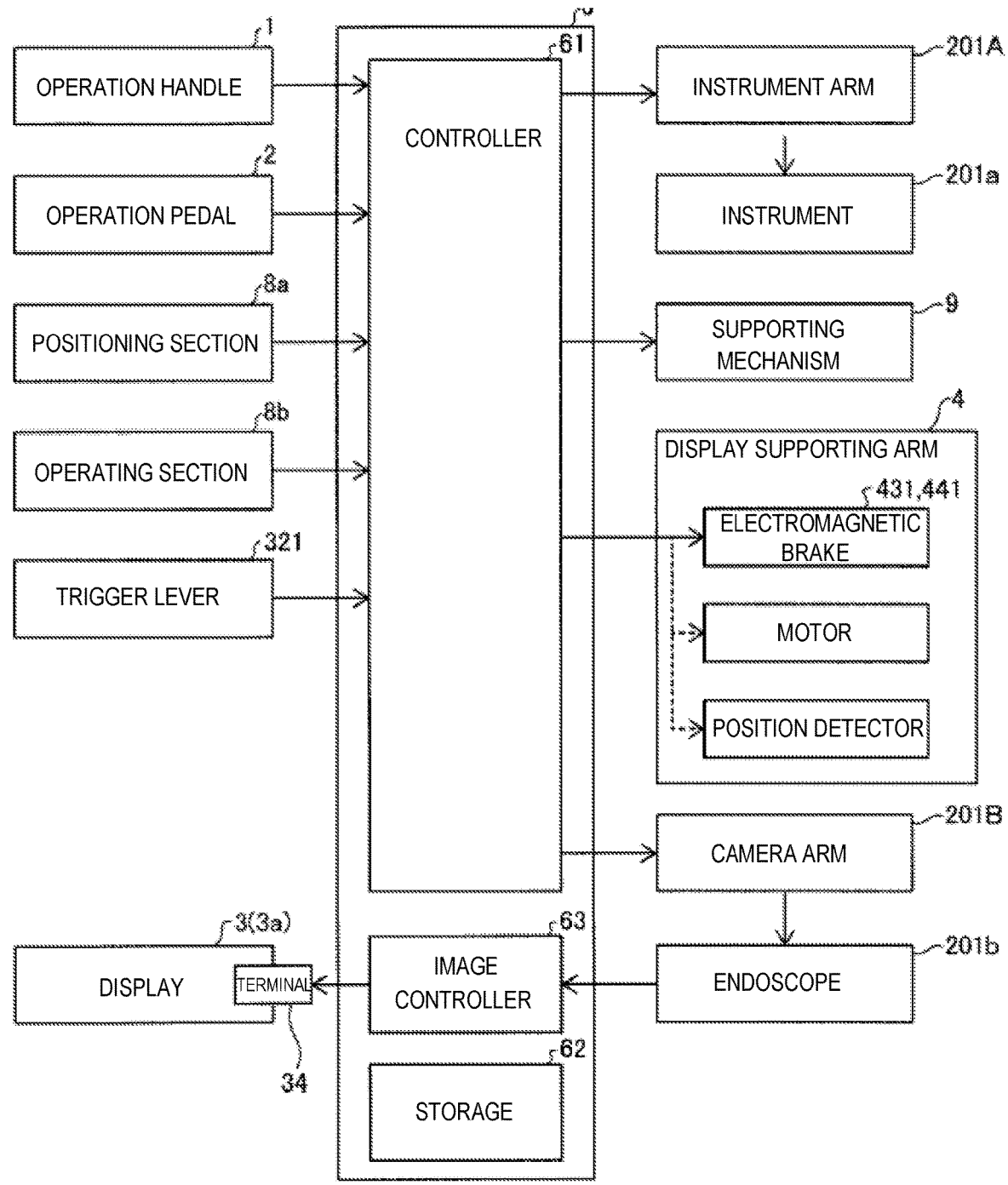
FIG. 4 is a block diagram illustrating a control-related configuration of the remote control apparatus.

As illustrated in FIGS. 2 and 4, the remote control apparatus 100 includes operation handles 1, an operation pedal section 2, a display supporting arm 4 supporting a display 3 or a display device, an armrest 5 supporting the arms of the operator O, and a control apparatus 6, and a base 7. The remote control apparatus 100 further includes a positioning section 8a, an operating section 8b, and a supporting mechanism 9. The supporting mechanism 9 supports the operation handles 1 and armrest 5.

The operation handles 1 are provided in order to remotely operate medical equipment held by the surgical manipulators 201. Specifically, the operation handles 1 accept operations by the operator O for operating medical equipment (the instruments 201a and endoscope 201b). The operation handles 1 include a pair of operation handles 1 arranged side by side in the X direction. The right operation handle 1 (on the X2 side) of the pair of operation handles 1 is operated by the right hand of the operator O while the left operation handle 1 (on the X1 side) is operated by the left hand of the operator O.

The operation handles 1 are attached to a supporting section 91 of the supporting mechanism 9. The operation handles 1 extend from the back side (the Y2 side) of the remote operation apparatus 100 toward the front side (the Y1 side). Plural joints are provided between the supporting section 91 and each operation handle 1 so that the operation handles 1 move relative to the supporting section 91 in a predetermined three-dimensional operation range A (see FIGS. 5 and 6). Specifically, the operation handles 1 are configured so as to move relative to the supporting section 91, up and down (in the Z direction), right and left (in the X direction), and forward and backward (in the Y direction). Each joint between the supporting section 91 and operation handles 1 is provided with a not-illustrated position detector that detects the positional relationship between the joints. The position detector is an encoder, a resolver, or a potentiometer, for example. The position detector thereby detects the positions of the operation handles 1 relative to the supporting section 91.

The remote control apparatus 100 and patient-side system 200 constitute a master-slave system in terms of controlling motion of the instrument arms 201A and camera arm 201B. The operation handles 1 constitute an operating section on the master side in the master-slave system, and the instrument arms 201A grasping medical equipment and the camera arm 201B constitute an operating section on the slave side. When the operator O operates the operation handles 1, the motion of the instrument arms 201A or camera arm 201B is controlled so that the tips (the end effectors of the instruments 201a) of the instrument arms 201A and the tip (the endoscope 201b) of the camera arm 201B move following the movement of the operation handles 1.

The patient-side system 200 controls the motion of the instrument arms 201A in accordance with the set motion scaling ratio. When the motion scaling ratio is set to ½, for example, the end effectors of the instruments 201a move ½ of the movement distance of the operation handles 1. This allows for precise fine surgery. The operation handles 1 are attached to the base 7 and extend toward the operator O in the Y direction.

The operation pedal section 2 includes pedals operable by a foot of the operator O. Each pedal is assigned to a specific function. One of such functions is to input a switching instruction to change the target to be controlled by the operation handles 1 among the plural instrument arms 201A and camera arm 201B. In order to change the field of view during surgery, the operator O operates the operation pedal section 2 for switching the target to be controlled by the operation handles 1 from the instrument arm 201A to the camera arm 201B and then operates the operation handles 1 to move the endoscope 201b. After moving the endoscope 201b, the operator O operates the operation pedal section 2 to return the target to be controlled by the operation handles 1 from the camera arm 201B to the instrument arm 201A, continuing the surgery. The operation pedal section 2 is placed in lower part so as to be operable by feet. The operation pedal section 2 is movable in the Y direction.

Another function of the operation pedal section 2 is to input an instruction to perform an action of the instrument 201a attached to the tip of each instrument arm 201A. The operation pedal section 2 is able to input an action to cause an instrument 201a to cut or coagulate a surgery site. Operating the operation pedal section 2 applies voltage for cutting or voltage for coagulation to the instrument 201a.

Figure 12:
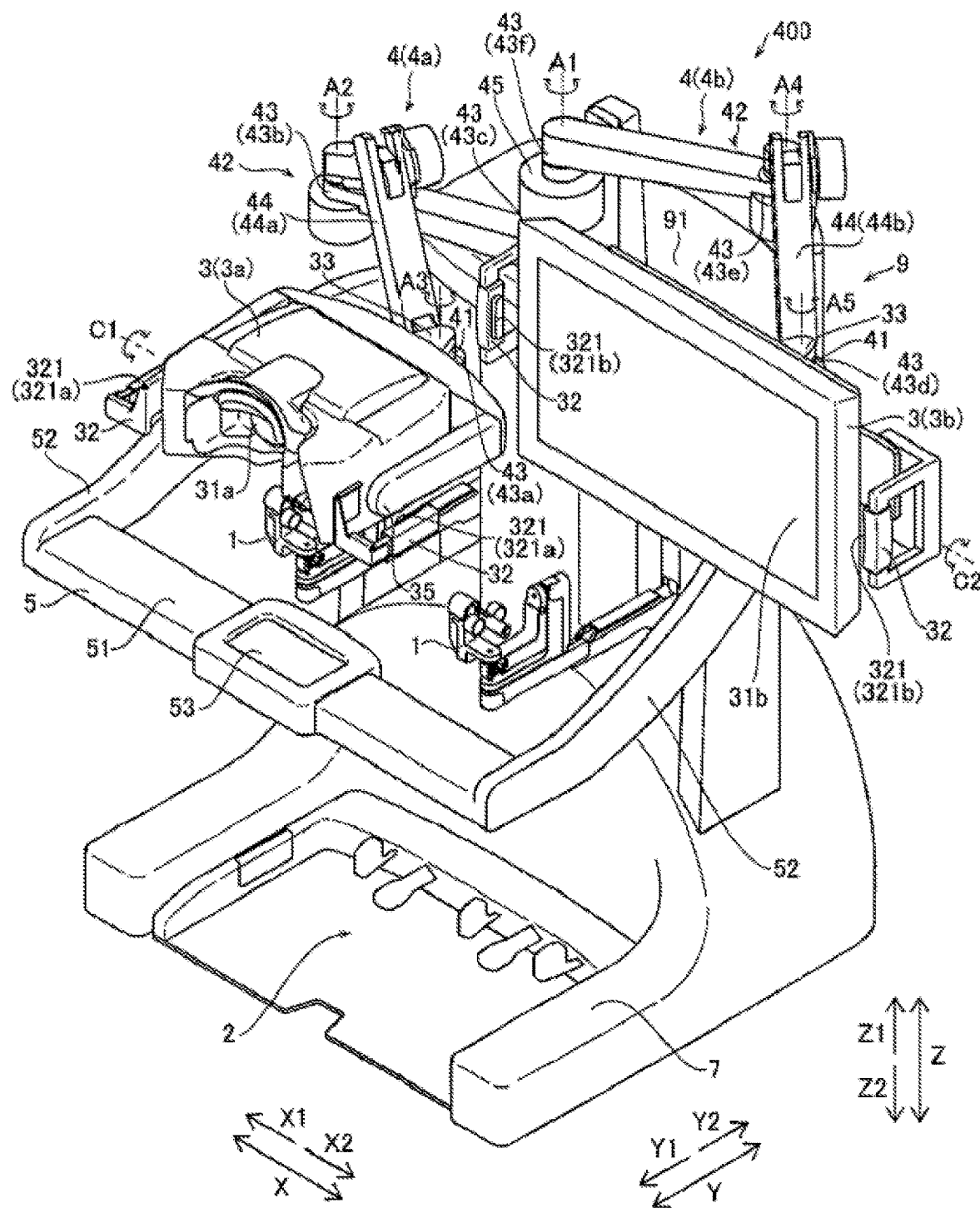
FIG. 12 is a perspective view illustrating a remote control apparatus according to a second embodiment.

The display 3 displays an image captured by the endoscope 201b. The display 3 includes a scope type display 3a or a non-scope type display 3b (see FIG. 12). The scope type display 3a is a display that the operator O looks into. The non-scope type display 3b is a concept including an open-type display that the operator O looks at without looking into and that has a flat screen, such as a normal personal computer display. The scope and non-scope type displays 3a and 3b are selectively attachable to the remote control apparatus 100. In the example illustrated in FIG. 2, the scope type display 3a is mounted on the remote control apparatus 100. As illustrated in FIG. 2, the scope type display 3a includes a display 31a, a grip section 32, an attachment section 33, a terminal 34 (see FIG. 4), and an angle adjustment joint 35. The non-scope type display 3b includes a display 31b, a grip section 32, an attachment section 33, a terminal 34 (see FIG. 4), and an angle adjustment joint 35 as illustrated in FIG. 12. The attachment section 33 of the scope and non-scope type display 3a or 3b is attachable to the mounting section 41 of the display supporting arm 4 of the remote control apparatus 100. In other words, the scope or non-scope type display 3a or 3b mounted on the remote control apparatus 100 is configured to be supported by the display supporting arm 4. This allows the remote control apparatus 100 to be used as either an immersive remote control apparatus or an open-type remote control apparatus. The remote control apparatus 100 is versatile in terms of the display 3.

Surgery often takes several hours. Surgeons who work for a long time with an immersive remote control apparatus sometimes experience a sense of isolation. Switching the remote control apparatus 100 to an open-type remote control apparatus before or during surgery makes surgeons more likely to have a sense of performing the surgery within a team.

The display of the remote control apparatus is versatile and expandable. If the display is broken or damaged, it is therefore only necessary to repair the display, and it is unnecessary to replace the entire apparatus. Moreover, the display can be upgraded without replacing the entire apparatus each time a higher definition or a higher quality display is developed. The operator can select a display of a favorite maker and favorite specifications (size, shape, type of operation panel, and the like).

The terminal 34 includes a terminal capable of transmitting video, such as a serial digital interface (SDI) terminal, an analogue component terminal, a high-definition multimedia interface (HDMI, registered trademark) terminal, or a universal serial bus (USB) terminal. The terminal 34 is connected to the control apparatus 6. By connecting connection wire to the terminal 34, the display 3 receives image information transmitted from the control apparatus 6. The display 3 is dismounted from the remote control apparatus 100 when the connection wire from the terminal 34 is disconnected.

When the scope type display 3a is mounted, 3D image captured by the endoscope 201b held by the camera arm 201B of the patient-side system 200 is displayed on the scope type display 3a. When the non-scope type display 3b is mounted, 3D image captured by the endoscope 201b provided to the patient-side system 200 is displayed on the non-scope type display 3b. When the non-scope type display 3b is mounted, 2D image captured by the endoscope 201b provided to the patient-side system 200 may be displayed on the non-scope type display 3b.

The scope type display 3a is a viewer that the operator O looks into. The scope type display 3a displays an image for the right eye of the operator O and an image for the left eye. The scope type display 3a is a stereoscope, for example. The display 31a includes a display for the right eye and a display for the left eye. When the operator O is looking into the display 31a, the display for the right eye cannot seen by the left eye while the display for the left cannot be seen by the right eye. The display 31a is composed of a liquid crystal display, an organic EL display, or the like. The display 31a may be a projection-type display.

The non-scope type display 3b is an open-type display that the operator O is able to see without looking into and is a direct-view-type display. The display 31b of the non-scope type display 3b includes a flat or curved screen. The display 31b can be a display with a diagonal of 10 to 90 inches, for example. Considering the balance between sufficient visibility of the surgical field and easy replacement, the display 31b preferably has a diagonal of 15 to 30 inches. The display 31b is composed of a liquid crystal display, an organic EL display, or the like. The display 31b can be a projection-type display. The non-scope type display 3b may employ a publicly-known stereoscopy in order for the operator O to stereoscopically view an image captured by the endoscope 201b, such as a method using polarization glasses or a method using active shutter glasses.

The grip section 32 is gripped when the display 3 is mounted, dismounted, or moved. The grip section 32 can be gripped with one hand. The grip section 32 has a grip, recessed, or protrusion shape. The grip section 32 is provided on a lateral side or back side of the display 3 so as not to interfere with viewing the display 31a (31b). The grip section 32 can be gripped with one hand, and the grip section 32 may include plural grip sections 32. For example, the grip sections 32 may be provided on both sides of the display 3 as illustrated in FIG. 2, for example, so that the operator O sitting in front of the display 3 can grip any grip section 32 with either right or left hand. Each grip section 32 includes a trigger lever 321. The trigger lever 321 is an example of an unlocking mechanism.

Figure 8A:
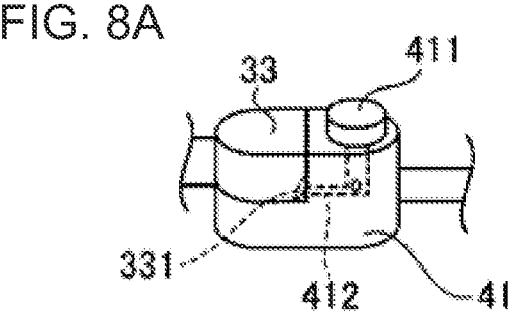
FIGS. 8A to 8C are schematic views for explaining a first example of a display engaging mechanism and an unlocking mechanism of the remote control apparatus according to a first embodiment.

The attachment section 33 is attached to the mounting section 41 of the display supporting arm 4. The mounting section 41 is detachably attached selectively to the scope or non-scope type display 3a or 3b, for example. The attachment section 33 includes an engagement section 331 as illustrated in a first example of FIGS. 8A to 8C. The mounting section 41 includes a release button 411 and an engagement section 412. As illustrated in FIG. 8A, in a fixed state, the engagement section 331 of the attachment section 33 is engaged with the engagement section 412 of the mounting section 41, so that the attachment section 33 is locked with the mounting section 41 of the display supporting arm 4. The display 3 is thereby fixed and supported by the display supporting arm 4. In other words, the engagement sections 331 and 412 constitute a display engaging mechanism to fix the display 3 (the scope or non-scope type display 3a or 3b).

Figure 8B:
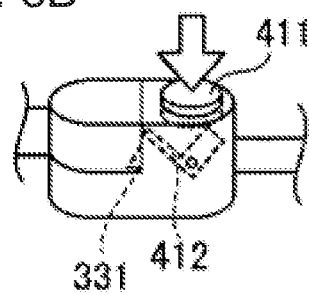

As illustrated in FIG. 8B, when the release button 441 is pressed down, the engagement section 412 moves and disengages from the engagement section 331. The engagement section 33 is thereby unlocked from the mounting section 41. The release button 411 functions as a disengaging mechanism that releases the engagement by the display engaging mechanism composed of the engagement sections 331 and 412. The disengaging mechanism is configured to release the engagement by the display engaging mechanism, with an action of force downward in the vertical direction. The disengaging mechanism thereby easily releases the engagement by the display engaging mechanism.

Figure 8C:
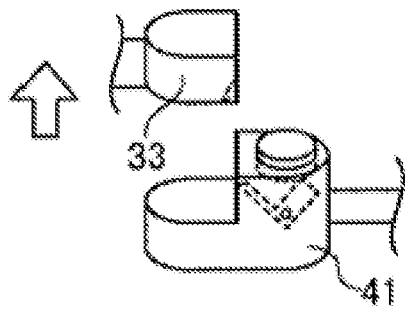

As illustrated in FIG. 8C, the grip section 32 of the display 3 is operated upward in the vertical direction while the disengaging mechanism is acting downward in the vertical direction, so that the display 3 is dismounted from the remote control apparatus 100. In such a manner, the display 3 is dismounted by performing the releasing operation downward in the vertical direction and the operation of raising the grip section upward in the vertical direction, that produce forces in the opposite directions. The display 3 is therefore dismounted stably and safely. The display 3 can be dismounted upward with space away from the display supporting arm 4, not interfering with the operation handles 1 located underneath.

Figure 9A:
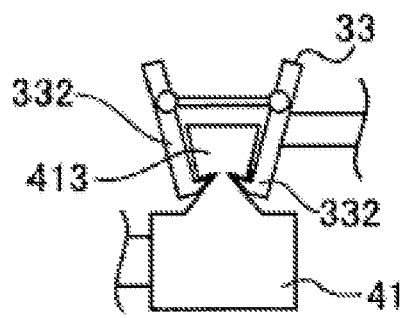
FIGS. 9A to 9C are schematic views for explaining a second example of the display engaging mechanism and unlocking mechanism of the remote control apparatus according to a first embodiment.
Figure 9B:
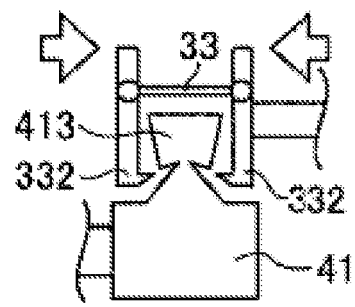
Figure 9C:
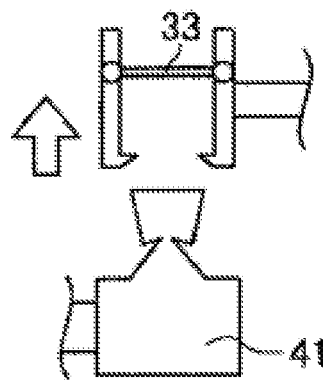

The display engaging mechanism and disengaging mechanism may have another configuration and may be configured as illustrated in FIGS. 9A to 9C as a second example. The attachment section 33 includes an engagement section 332 as shown in FIGS. 9A to 9C. The mounting section 41 includes an engagement section 413. As illustrated in FIG. 9A, in the fixed state, the engagement section 332 of the attachment section 33 is engaged with the engagement section 413 of the mounting section 41, so that the attachment section 33 is locked with the mounting section 41 of the display supporting arm 4. Specifically, the engagement section 332 sandwiches and grips the engagement section 413. The display 3 is thereby fixed to and supported by the display supporting arm 4. In other words, the engagement sections 332 and 413 constitute the display engaging mechanism to fix the display 3 (the scope or non-scope type display 3a or 3b).

As illustrated in FIG. 9B, when the engagement section 332 is pressed on both sides, the grip by the engagement section 332 is released, so that the engagement section 332 disengages from the engagement section 413. The attachment section 33 is thereby unfixed (unlocked) from the mounting section 41. As illustrated in FIG. 9C, the grip sections 32 is operated upward in the vertical direction while the attachment section 33 is unlocked. The display 3 is thereby dismounted from the remote operation apparatus 100.

Figure 10A:
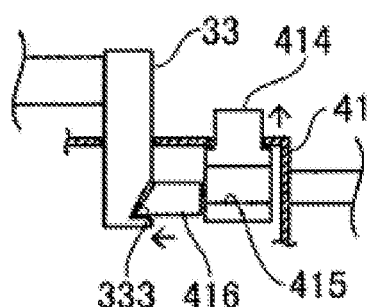
FIGS. 10A to 10C are schematic views for explaining a third example of the display engaging mechanism and unlocking mechanism of the remote control apparatus according to a first embodiment.
Figure 10B:
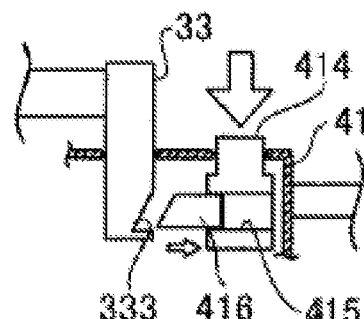
Figure 10C:
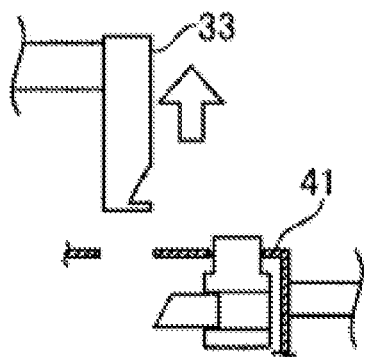

The display engaging mechanism and release mechanism may have still another configuration as illustrated in FIGS. 10A to 10C as a third example. The attachment section 33 includes a notch 333 as shown in FIGS. 10A to 10C. The mounting section 41 includes a release button 414, a fitting section 415, and an engagement section 416. As illustrated in FIG. 10A, the release button 414 is energized upward in the vertical direction by a spring or the like. The engagement section 416 is energized in a horizontal direction away from the fitting section 415. The vertical movement of the release button 414 and the horizontal movement of the engagement section 416 work in conjunction with a gear and the like.

In the fixed state, the notch 333 of the attachment section 33 is engaged with the engagement section 416 of the mounting section 41, so that the attachment section 33 is locked with the mounting section 41 of the display supporting arm 4. The display 3 is thereby fixed to and supported by the display supporting arm 4. In other words, the notch 333 and engagement section 416 constitute the display engaging mechanism to fix the display 3 (the scope or non-scope type display 3a or 3b).

As illustrated in FIG. 10B, when the release button 414 is pressed down, the fitting section 415 moves downward. The engagement section 416 then moves toward the fitting section 415 and fits into the fitting section 415. The notch 333 thereby disengages from the engagement section 416. The attachment section 33 is then unlocked from the mounting section 41. In other words, the release button 414 functions as the disengaging mechanism to release the engagement by the display engaging mechanism composed of the notch 333 and engagement section 416. The disengaging mechanism releases the engagement by the display engaging mechanism by an action of vertically downward force.

As illustrated in FIG. 10C, the grip section 32 of the display 3 is operated upward in the vertical direction while the attachment section 33 is unlocked. The display 3 is thereby dismounted from the remote operation apparatus 100.

Having a lower-side length larger than an upper-side length, the engagement section 416 has a slope. When the attachment section 33 is pressed vertically downward against the mounting section 41, the attachment section 33 comes into contact with the slope of the engagement section 416 and presses the engagement section 416 into the fitting section 415 in the horizontal direction. When the attachment section 33 moves to a predetermined position, the engagement section 416 fits into the notch 333 and is locked in the fixed state.

The display supporting arm 4 supports the display 3 as illustrated in FIG. 2. The display supporting arm 4 includes the mounting section 41, an arm section 42, plural joints 43, and a parallel link mechanism 44. At an end of the display supporting arm 4, the mounting section 41 is provided. The other end thereof is supported by a column 45. The column 45 is fixed to a supporting section 91 of the supporting mechanism 9. The display 3 is thus supported by the supporting section 91. The display supporting arm 4 is rotatable around rotation axes A1, A2, and A3, which extend vertically. The display supporting arm 4 is configured so that the mounting section 41 is moved up and down by the parallel link mechanism 44. The mounting section 41 is thus supported with four degrees of freedom by the arm section 42.

The display supporting arm 4 includes joints 43a, 43b, and 43c as the joints 43. The joints 43a to 43c are respectively provided with electromagnetic brakes 431a, 431b, and 431c as electromagnetic brakes 431. The parallel link mechanism 44 includes an electromagnetic brake 441a as an electromagnetic brake 441. The joints 43a to 43c and parallel link mechanism 44 are examples of a joint, and the electromagnetic brakes 431a to 431c and 441a are examples of a locking mechanism.

As illustrated in FIG. 2, the scope type display 3a is attached to the display supporting arm 4. In other words, the display supporting arm 4 supports the scope type display 3a.

Figure 3:
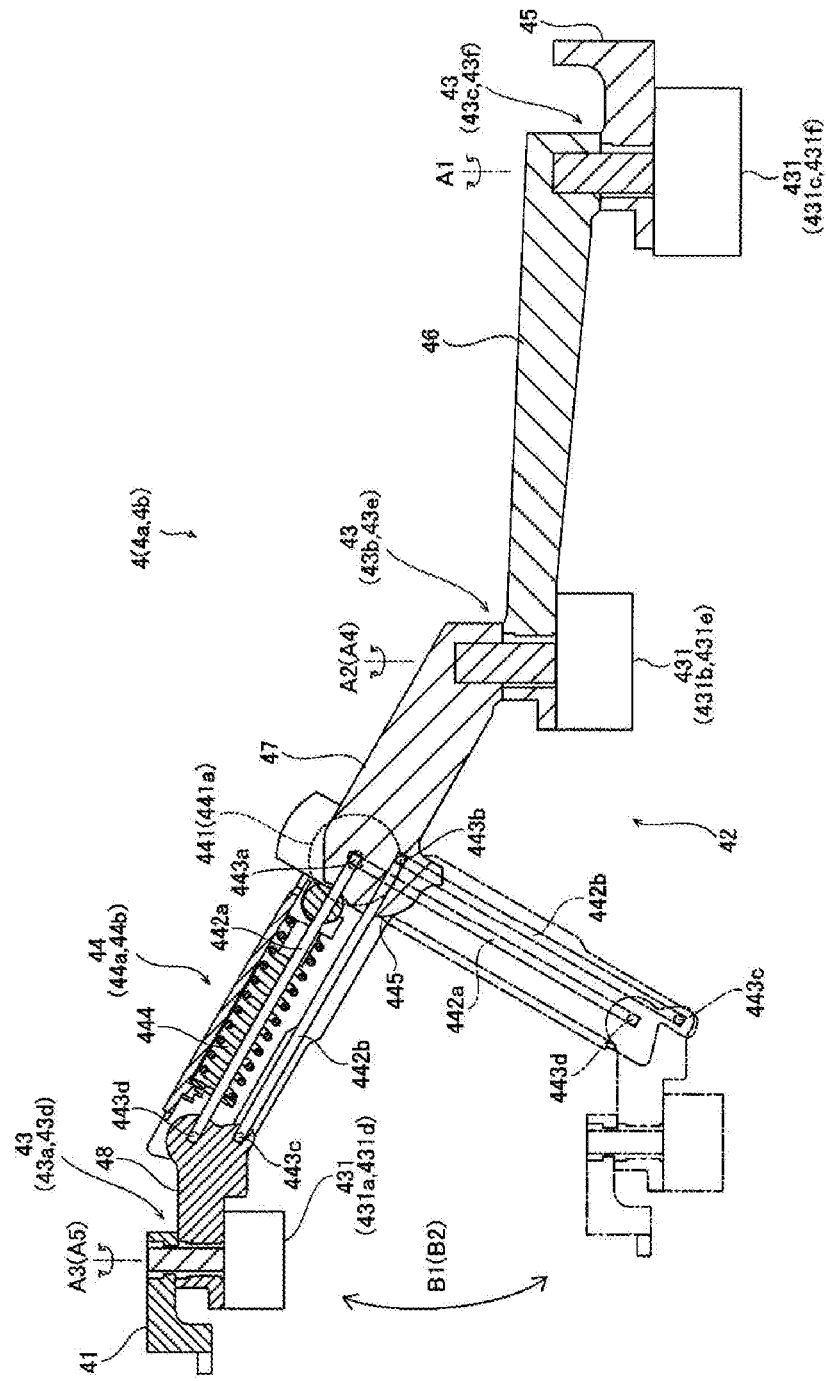
FIG. 3 is a view illustrating a display supporting arm of the remote control apparatus.

The joint 43a connects the mounting section 41 and a third link 48 so that the mounting section 41 and third link 48 rotate around the rotation axis A3. The joint 43b connects a second link 47 and a first link 46 so that the second and first links 47 and 46 rotate around the rotation axis A2. The joint 43c connects the first link 46 and column 45 so that the first link 46 and column 45 rotate around the rotation axis A1. As illustrated in FIG. 3, the parallel link mechanism 44 connects the third and second links 48 and 47 so as to rotate in B1 direction around a horizontal rotation axis orthogonal to the rotation axes A1 to A3.

The electromagnetic brakes 431 are configured to lock the joints 43. Specifically, while not energized, each electromagnetic brake 431 presses at least one of two links connected at the corresponding rotation axis to prevent motion of the joint 43 into the locked state. While energized, magnetic force generated by the electromagnetic coil separates the electromagnetic brake 431 from the pressed link, thus unlocking the joint 43. The electromagnetic brake 431a presses the mounting section 41 at the rotation axis A3 to lock the joint 43a. The electromagnetic brake 431b presses the second link 47 at the rotation axis A2 to lock the joint 43b. The electromagnetic brake 431c presses the first link 46 at the rotation axis A1 to lock the joint 43c.

The electromagnetic brake 441a is configured to lock the parallel link mechanism 44. Specifically, while not energized, the electromagnetic brake 441a presses the parallel link mechanism 44 to lock the same. While energized, the electromagnetic brake 441a unlocks the parallel link mechanism 44.

The grip section 32 of the display 3 is provided with the trigger lever 321 as the unlocking mechanism to release the lock of the electromagnetic brakes 431 and 441. When the trigger lever 321 is pressed down, the corresponding electromagnetic brake 431 or 441 is energized to release the lock. The trigger lever 321 is operated by the operator O to unlock the corresponding joint (at least one of the joints 43a to 43c and parallel link mechanism 44).

The trigger lever 321 includes two trigger levers 321 disposed on the right and left sides of the display 3 by way of example. As illustrated in FIG. 2, trigger levers 321a are individually provided on the right and left side of the scope type display 3a. As illustrated in FIG. 12, trigger levers 321b are individually provided on the right and left sides of the non-scope type display 3b. Each trigger lever 321 is gripped with the grip section 32 (pressing operation) for the unlocking operation. When both of the right and left trigger levers 321 are pressed, all the joints (the joints 43a to 43c and parallel link mechanism 44) are unlocked. When either the right or left lever 321 is not pressed or any of the right and left levers 321 is not pressed, any joint is not unlocked. In such a configuration, the joints cannot be unlocked even if one of the trigger levers 321 is touched and is pressed accidentally. The joints 43 and parallel link mechanism 44 are prevented from being unlocked accidentally.

While any of the right and left trigger levers 321 is not pressed, all the joints of the display supporting arm 4 are locked. This prevents the position of the display 3 from shifting during operation of the operation handles 1. When the operation for the operation handles 1 is stopped and both of the right and left trigger levers 321 are pressed, all the joints of the display supporting arm 4 are unlocked, so that the operator O can arbitrarily change the position of the display 3. The operator O is able to change the display 3 to any position easily. Since the display 3 is supported by the display supporting arm 4 composed of plural joints and links as described above, the display 3 is adjustable in a wide range and can move to any place in a linear manner, compared with a mechanism just capable of adjusting the angle and the positions in the height and depth directions, of a display as described in Patent Literature 1. When the display 3 is the scope type display 3a, that the operator O looks into, the operator O can press the both right and left trigger levers 32a and move the scope type display 3a to a desired position while looking into the scope type display 3a. The remote control apparatus 100 therefore allows the operator O to change his/her posture sensuously and quickly compared with the case where the operator checks the posture with his/her face affixed on the display 3 each time the operator separately sets the angle, height, and depth of the display 3.

As described above, with this remote control apparatus 100, the operator can easily change the posture in a wide range of adjustment during long surgery. It is therefore possible to reduce the operator's feeling of fatigue and ill effects on the operator's health of remaining in the same posture.

The display supporting arm 4 is placed on the opposite side of the display 3 from the operator O. The display supporting arm 4 is placed in the back side (on the Y2 side) of the display 3. This prevents the display supporting arm 4 and the operator O from interfering with each other, effectively increasing the freedom of movement of the display supporting arm 4.

The parallel link mechanism 44 includes the electromagnetic brake 441, links 442a and 442b, pivots 443a, 443b, 443c, and 443d, a spring 444, and a base section 445 as illustrated in FIG. 3. The parallel link mechanism 44 is configured to translate the display 3 attached to the mounting section 41 up and down. In other words, the parallel link mechanism 44 is configured to move the display 3 up and down without changing the angle of the display screen of the display 3.

To be specific, in the parallel link mechanism 44, the link 442a is rotatably connected to the pivots 443a and 443d. The link 442b is rotatably connected to the pivots 443b and 443c. The links 442a and 442b are placed parallel to each other. The pivots 443a and 443b are disposed one above the other on a line parallel to the vertical direction with a predetermined interval therebetween. The pivots 443c and 443d are disposed one above the other on a line parallel to the vertical direction with a predetermined interval therebetween. The pivots 443a to 443d are thus located on vertices of a parallelogram. In other words, the line connecting the pivots 443a and 443b is parallel to the line connecting the pivots 443d and 443c. The line connecting the pivots 443d and 443c is therefore always parallel to the vertical direction. When the mounting section 41 moves up and down, the angle of the mounting section 41 to the vertical direction is kept constant. The horizontal position of the mounting section 41 is slightly shifted when the mounting section 41 is moved up or down by the parallel link mechanism 44.

The electromagnetic brake 441 is attached to the pivot 443a. The electromagnetic brake 441 presses the second link 47 and parallel link mechanism 44 to lock the rotation of the pivot 443a. When the rotation of the pivot 443a is locked, the rotation of the pivots 443b to 443d, which are connected thereto by the links 442a and 442b, is also locked.

The spring 444 is provided to press the base section 445 of the second link 47. The base section 445 has a protruding bow-like shape. When the end of the spring 444 on the second link 47 side presses the bow-like base section 445, the end of the spring 444 tries to move upward along the bow-like base section 445, generating a force to rotate upward the end of the parallel link mechanism 44 opposite to the second link 47. Even if the display 3 needs to move against the gravity, therefore, the operator O is able to move upward easily.

The angle adjustment joint 35 is provided between the display supporting arm 4 and display 3 separately from the joints 43 and parallel link mechanism 44 of the display supporting arm 4. The angle adjustment joint 35 adjusts the angle of the display screen of the display 3. The angle adjustment joint 35 includes an angle adjustment joint 35a and an angle adjustment joint 35b. The angle adjustment joint 35a supports the scope type display 3a so that the scope type display 3a is rotatable in a direction C1 (see FIG. 2). The angle adjustment joint 35b supports the non-scope type display 3b so that the non-scope type display 3b is rotatable in a direction C2 (see FIG. 12). The angle adjustment joint 35 is provided on the display 3 side when the display 3 is dismounted from the display supporting arm 4. The angle of the display screen of the display 3 can be thereby changed independently. This facilitates adjustment of the angle of the display screen of the display 3.

The positioning of the display supporting arm 4 may be changed manually by the operator O or others or may be changed under movement control by a driver including a motor, a position detector, such as an encoder, and a brake. The display supporting arm 4 can be manually moved or electrically moved. When the display 3 is manually moved with the brake released, the motor also operates following the motion of the display 3 manually operated, and the position of the display 3 can be stored by the position detector. In the case of electrically moving the display 3, motions may be instructed with a handheld or the like. The handheld may be provided with a release button to release the brake. Alternatively, the brake may be released automatically by operating a movement direction instruction button. The handheld may be composed of a remote controller including plural buttons or a teaching pendant, for example. In addition, the position of the display 3 (the positioning of the display supporting arm 4) may be stored for each surgeon. The position of the display 3 (the positioning of the display supporting arm 4) may be changed in cooperation with transition between the standing position and sitting position.

Figure 5:
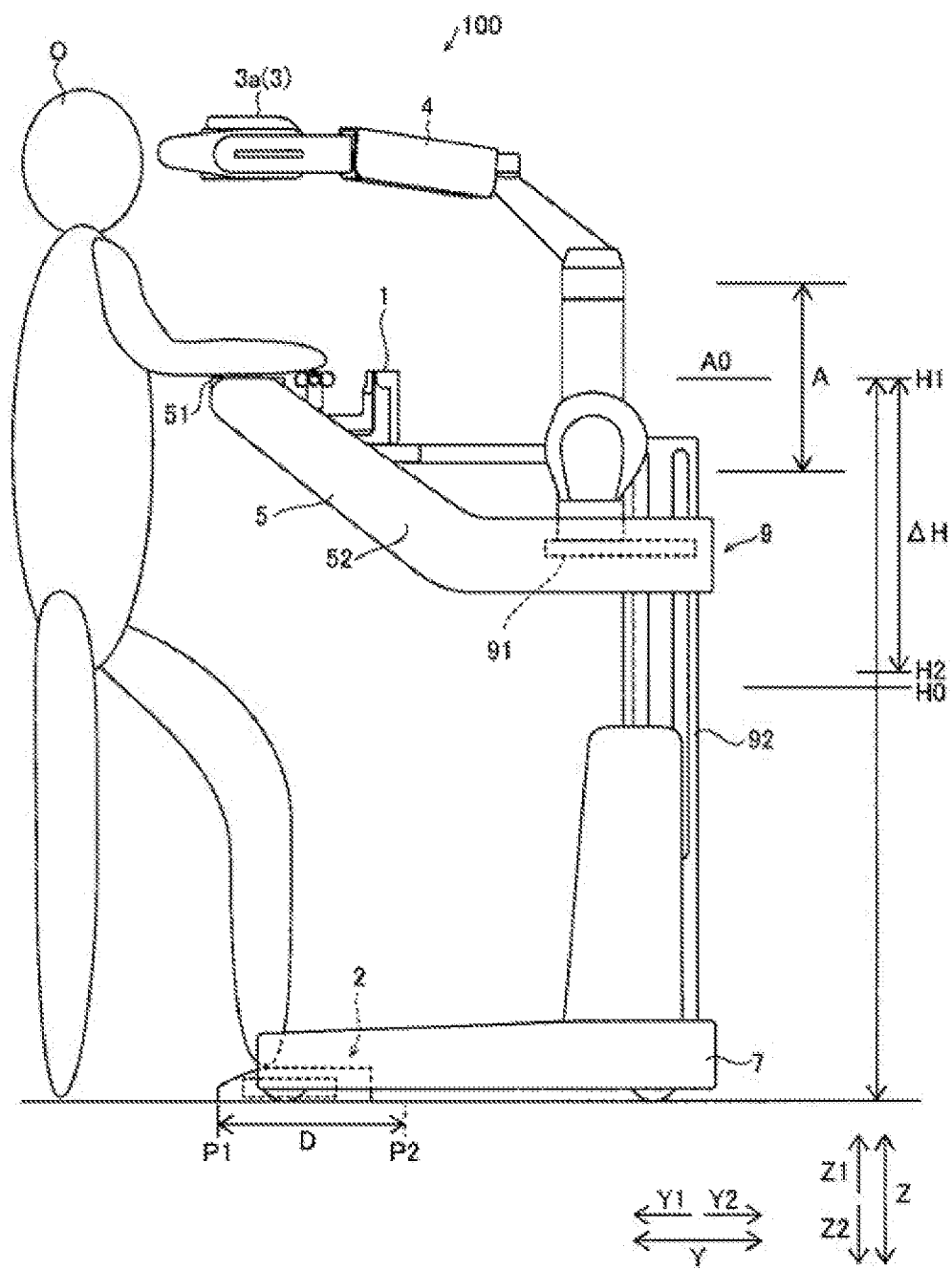
FIG. 5 is a side view illustrating a first configuration of the remote control apparatus.
Figure 6:
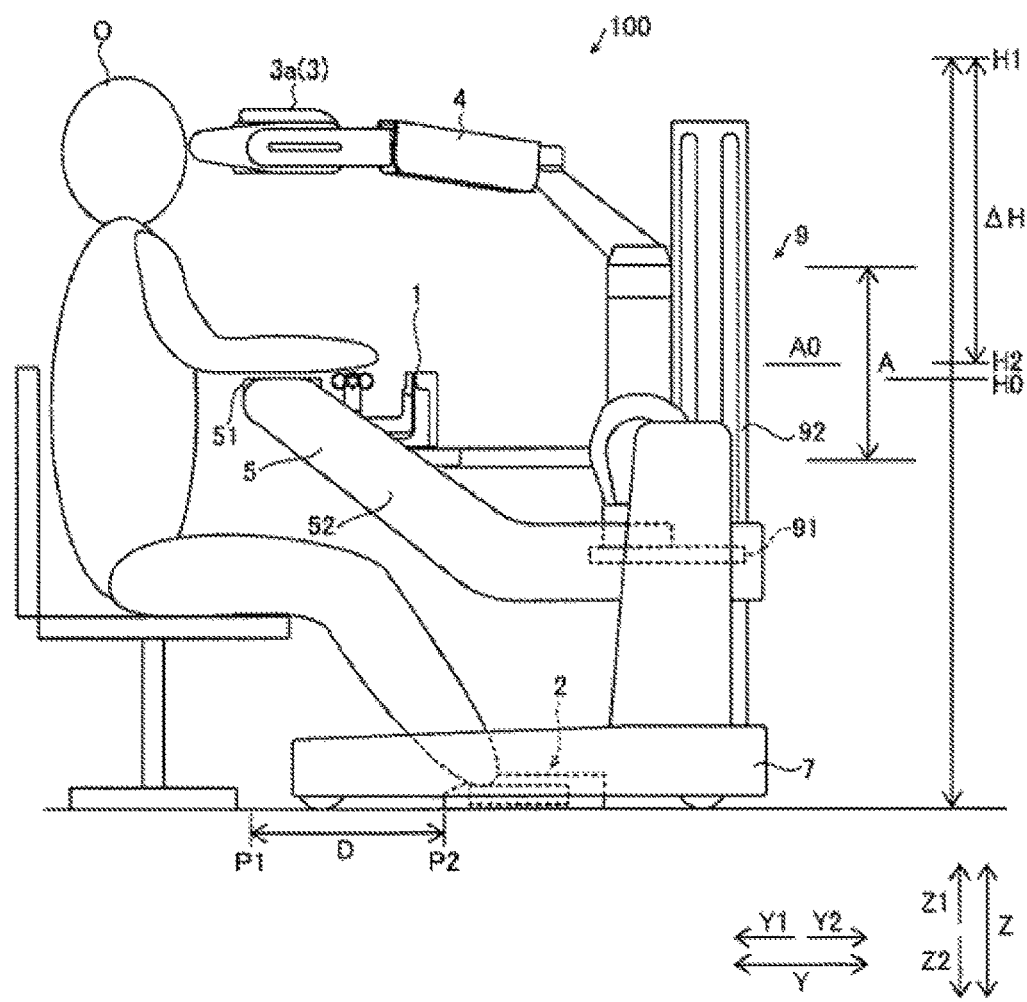
FIG. 6 is a side view illustrating a second configuration of the remote control apparatus.

The armrest 5 supports arms of the operator O. The armrest 5 includes an arm supporting section 51 and a pair of connecting sections 52, and an operating section 53. The arm supporting section 51 is located in front (on the Y1 side) of the operation handles 1 and is configured to support the arms of the operator O. This stabilizes the arms of the operator O, so that the operator O can stably operate the operation handles 1. Even when the end effectors need to be moved finely, the operator O performs stabilized operation with elbows and the like on the arm rest 5. The operator O feels less strain even in long surgery. The arm supporting section 51 extends in the X direction. The pair of connecting sections 52 are provided to both ends of the arm supporting section 51 so as to sandwich the arm supporting section 51 in the X direction. The connecting sections 52 support the arm supporting section 51. The connecting sections 52 extend in the Y direction. The end of each connecting section 52 on the Y1 side is connected to the arm supporting section 51. The ends of the connecting sections 52 on the Y2 side are connected to the supporting section 91 of the supporting mechanism 9. The armrest 5 is thus supported by the supporting mechanism 9. As illustrated in FIG. 2, the connecting sections 52 may be extended downward from the back side (the Y2 side) to the front side (the Y1 side). As illustrated in FIGS. 5 and 6, the connecting sections 52 may be extended upward from the back side (the Y2 side) to the front side (the Y1 side). Alternatively, the connecting sections 52 may be extended in the horizontal direction. The operating section 53 enables operation for settings of the remote control apparatus 100. For example, the operating section 53 enables operation for positioning the remote control apparatus 100. In this case, the operating section 53 functions as the positioning section 8a. The operating section 53 may function as the operating section 8b. The operating section 53 includes a touch panel, for example.

As illustrated in FIG. 4, the control apparatus 6 includes a controller 61, a storage 62, and an image controller 63, for example. The controller 61 includes a calculator such as a CPU. The storage 62 includes a memory, such as a ROM and a RAM. The control apparatus 6 may be composed of a single controller performing centralized control or may be composed of plural controllers that perform decentralized control in cooperation with each other. The controller 61 determines whether the action mode instruction inputted by the operation handles 1 is to be executed by the instruments 201a or to be executed by the endoscope 201b, depending on the state of the operation pedal section 2. When determining that the action mode instruction inputted by the operation handles 1 is to be executed by the instruments 201a, the controller 61 transmits the action mode instruction to the instrument arm 201A. The instrument arms 201A are thereby driven for control of motions of the instruments 201a attached to the instrument arms 201A.

When determining that the action mode instruction inputted by the operation handles 1 is to be executed by the endoscope 201b, the controller 61 transmits the action mode instruction to the camera arm 201B. The camera arm 201B is thereby driven for control of motions of the endoscope 201b attached to the camera arm 201B.

The storage 62 stores control programs corresponding to the types of the instruments 201a, for example. The controller 61 reads the stored control programs according to the types of the attached instruments 201a. The action mode instructions from the operation handles 1 and/or the operation pedal section 2 of the remote control apparatus 100 thereby causes the respective instruments 201a to perform proper motions.

The image controller 63 transmits an image acquired by the endoscope 201b to the terminal 34 of the display 3. The image controller 63 modifies the image if necessary.

The positioning section 8a receives operations to move up and down the operation handles 1, the display 3 supported by the display supporting arm 4, and the arm rest 5. The positioning section 8a also receives operations to transform the remote control apparatus 100 between a first configuration and a second configuration.

The positioning section 8a is an operating section that receives a configuration change instruction to change the configuration of the remote control apparatus 100 to the standing position (the first configuration) or the sitting position (the second configuration). The positioning section 8a includes plural operation buttons.

The supporting mechanism 9 includes the supporting section 91 and the driver 92. The supporting section 91 supports the operation handles 1 and armrest 5. The supporting section 91 supports the display 3 through the display supporting arm 4. The driver 92 is configured to move the supporting section 91 up and down. To be specific, the driver 92 includes a motor and an encoder, for example, and moves the supporting section 91 up and down under control by the control apparatus 61. The supporting mechanism 9 may allow the operator O or others to manually change the positioning. In addition, the driver 92 of the supporting mechanism 9 may be driven pneumatically or hydraulically. The armrest 5 may be rotated relative to the supporting mechanism 9 for adjustment of the position. For example, the armrest 5 may be rotated around the rotation axis along the X direction.

The supporting mechanism 9 is configured to transition between a first mode and a second mode. In the first mode (see FIG. 5), the operation handles 1 which are positioned at a neutral position A0 of the operation range A are placed and held at a height position H1, which is 85 cm or more above the floor surface on which the remote control apparatus 100 is installed, for example. In the second mode (see FIG. 6), the operation handles 1 which are positioned at the neutral position A0 of the operation range A are placed and held at a height position H2, which is 48 cm or more below the height position H1. When the operation handles 1 which are positioned at the neutral position A0 of the operation range A, are located at the height position H1 (85 cm or more above the floor surface), the operator O is able to operate the operation handles 1 while standing up. When the operation handles 1 which are positioned at the neutral position A0 of the operation range A are located at the height position H2 (48 cm or more below the height position H1), the operator O is able to operate the operation handles 1 while sitting down. The operator O is thus able to operate the remote control apparatus 100 in a desired posture. In addition, since the operation handles 1 are supported by the supporting mechanism 9, the operator O does not need to support the operation handles 1. This prevents an increase in strain on the operator O. The armrest 5 supporting the arms of the operator O further reduces the strain on the operator O and stabilizes the arms of the operator O. The operator O is therefore able to stably operate the operation handles 1.

The supporting mechanism 9 is configured to transition between the first mode (see FIG. 5), in which the operation handles 1 are held so that the operation range A of the operation handles 1 is within a clean area set at a predetermined height position or more above the floor surface on which the remote control apparatus 100 is installed, and the second mode (see FIG. 6), in which the operation handles 1 are held so that at least a part of the operation range A of the operation handles 1 is located below the clean area.

In operation rooms, clean technique is used in order to prevent surgical incision sites and medical equipment from being contaminated by pathogen, foreign matters, or the like. In the clean technique, a clean area and a contaminated area, which is other than the clean area, are defined. The area from the floor surface to a certain height position H where foreign matters including dust and grit are more likely to remain is treated as the contaminated area in principle and is eliminated from the clean area. This area lies from the floor surface to a height position of about 70 cm, for example. The clean area is therefore set to a height position of 70 cm or more above the floor surface on which the remote control apparatus 100 is installed, for example. Members of the surgical team including the operator O make sure that only sterile objects are placed in the clean area during surgery and perform sterilization for an object which is to be moved from the contaminated area to the clean area. Similarly, when the members of the surgical team including the operator O locate their hands in the contaminated area, the members sterilize their hands before directly touching objects located in the clean area. The operation handles 1 are treated as unclean objects. Even if the operation handles 1 are located in the clean area, the operator O never accesses the patient P without sterilization or use of drape while operating the operation handles 1.

When the operation handles 1 are located so that the operation range A of the operation handles 1 is within the clean area set at the predetermined height or more above the floor surface, the operator O is able to operate the operation handles 1 while keeping his/her hands inside the clean area. If the operation handles 1 are cleaned, for example, the hands of the operator O is kept clean. When the operation handles 1 are held so that at least a part of the operation range A of the operation handles 1 is located below the clean area, the sitting operator O is able to operate the operation handles 1 at the low position. The operator O is thus able to operate the remote control apparatus 100 in a desired posture. In addition, the operation handles 1 are supported by the supporting mechanism 9, and the operator O does not need to support the operation handles 1. This can prevent an increase in strain on the operator O.

The supporting mechanism 9 is also configured to allow for transition between the first mode (see FIG. 5), in which the operation handles 1 are held at the position suitable for the operator O to operate the operation handles 1 while standing up and the second mode (see FIG. 6) in which the operation handles 1 are held at the position suitable for the operator O to operate the operation handles 1 while sitting down. When the remote operation apparatus 100 is set to the first mode, the operator O can operate the operation handles 1 while standing up. When the remote operation apparatus 100 is set to the second mode, the operator O is able to operate the operation handles 1 while sitting down. The operator O is thus able to operate the remote control apparatus 100 in a desired posture. In addition, the operation handles 1 are supported by the supporting mechanism 9, and the operator O does not need to support the operation handles 1. This can reduce an increase in strain on the operator O.

The supporting mechanism 9 is configured to move both the operation handles 1 and armrest 5 up and down at transition between the first and second modes. Specifically, the supporting mechanism 9 is configured to integrally move the operation handles 1 and armrest 5 up and down at transition between the first and second modes. This requires less components than that in the case where members for moving the operation handles 1 and armrest 5 up and down are separately provided. It is therefore possible to simplify the apparatus configuration and prevent an increase in size of the apparatus. In addition, the supporting mechanism 9 is configured to move the display 3 supported by the display supporting arm 4 up and down at transmission between the first and second modes. The supporting mechanism 9 thus integrally moves the operation handles 1, armrest 5, and display 3 up and down at transition between the first and second modes.

The supporting mechanism 9 supports the display 3 that displays an image captured by the endoscope 201b and supports the display 3 so that the position of the display 3 relative to the operation handles 1 is changeable in each of the first and second modes. To be specific, the position of the display 3 is moved relative to the operation handles 1 by the display supporting arm 4 supported by the supporting mechanism 9. The position of the display 3 relative to the operation handles 1 can be therefore changed according to the physique and posture of the operator O. This can increase the versatility of the display 3.

Operation for the patient-side system 200 by the operation handles 1 is disabled at transformation between the first and second modes. To be specific, during transformation between the first and second modes, operation by the operation handles 1 is disabled, or transmission of action mode instructions is disabled. In other words, during transformation between the first and second modes, the control apparatus 61 does not transmit an action mode instruction to the patient-side system 200 even if the action mode instruction is transmitted from the operation handles 1. This prevents the patient-side system 200 from working when the operation handles 1 are operated accidentally during transformation between the first and second modes.

As illustrated in FIG. 5, when the remote control apparatus 100 is in the standing position (the first configuration), the operation handles 1 are positioned at a height suitable for the standing operator O to grip the operation handles 1 positioned at the neutral position A0 with the arms bent at substantially right angles. The display 3 is positioned at a height suitable for the standing operator O to look at the display 3. When the scope type display 3a is mounted, for example, the scope type display 3a is set at the same height as the eyes of the operator O.

When the area from the floor surface to a height position H of 70 cm is set to the contaminated area in a surgery room, the operation range A of the operation handles 1 is fully within the clean area 70 cm or more above the floor surface in the standing position mode (the first configuration) by designing based on a human model for ergonomics.

When the remote control apparatus 100 is in the standing position (the first configuration), the operation pedal section 2 is moved to a position P1 in the front side (in the Y1 side) of the remote control apparatus 100. In other words, the operation pedal section 2 is located to such a position that the standing operator O reaches the operation pedal section 2 with his/her foot while touching the operation handles 1 with his/her hands.

As illustrated in FIG. 6, when the remote control apparatus 100 is in the sitting position (the second configuration). The operation handles 1 are positioned at a height suitable for the operator O sitting in the chair to grip the operation handles 1 positioned at the neutral position A0 with his/her arms bent at substantially right angles. In addition, the display 3 is positioned at a height position suitable for the operator O sitting in the chair to look at the display 3. When the scope type display 3a is mounted, for example, the scope type display 3a is set at the same height as the eyes of the operator O. With the remote control apparatus 100, the operator O can execute surgery while sitting down in a long surgery. This can reduce fatigue of the operator O.

When the area from the floor surface to the height position H of 70 cm is set to the contaminated area in a surgery room, at least a part of the operation range A of the operation handles 1 is in the contaminated area in the sitting position mode (the second configuration) by designing based on human models for ergonomics.

When the remote control apparatus 100 is in the sitting position (the second configuration), the operation pedal section 2 is located to a position P2 in the back side (in the Y2e side) of the remote control apparatus 100. In other words, the operation pedal section 2 is located to such a position that the sitting operator O reaches the operation pedal section 2 with his/her feet while touching the operation handles 1 with his/her hands. The operation pedal section 2 is movable forward and backward by 300 mm or more (in the Y direction), for example. Preferably, the operation pedal section 2 is movable forward and backward by 350 mm or more (in the Y direction). The operation pedal section 2 can be therefore easily located to the positions suitable for the first and second configurations.

Specific dimensions and the like of the remote control apparatus 100 are designed using measurement data described in "1988 ANTHROPOMETRIC SURVEY OF U.S. ARMY PERSONNEL: METHODS AND SUMMARY STATISTICS (1988)".

The remote control apparatus 100 may be designed with reference to JIS standards. For example, "JIS Z8503-4: 2006 (ISO 11064-4: 2004), Ergonomic design of control centres, Part 4: Layout and dimensions of workstations" prescribes use of the 5th and 95th percentile human models.

The operation range A is defined as a region between 15 cm above and below the neutral position A0. The dimension of the operation range A in the height direction is defined as 30 cm. The operation range A is defined based on the dimensions of the motion range of surgical tools set to keep good operability of the surgical tools at laparoscopic surgery and the motion scaling ratio of the operation handles 1. The set motion range of the surgical tools has a dimension of 30 cm in the height direction, and the motion scaling ratio of the operation handles 1 is ½. The dimension of the operation range A in the height direction is therefore 30 cm based on the dimension of the motion range of the surgical tools in the height direction and the motion scaling ratio of the operation handles 1.

Figure 7A:
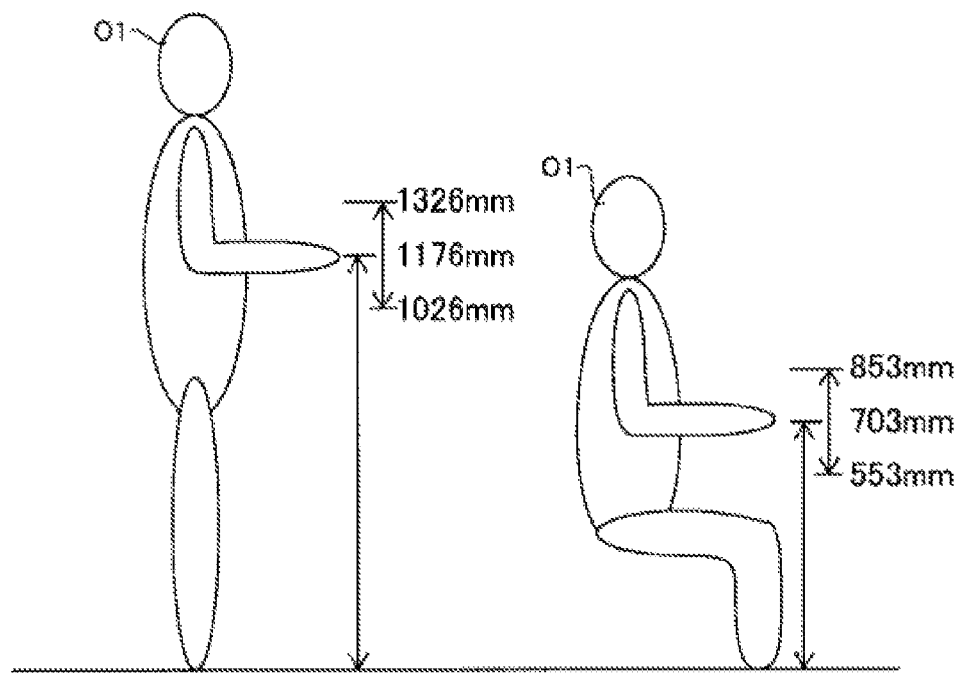
FIGS. 7A and 7B are views each illustrating a model of operators of the remote control apparatus.
Figure 7B:
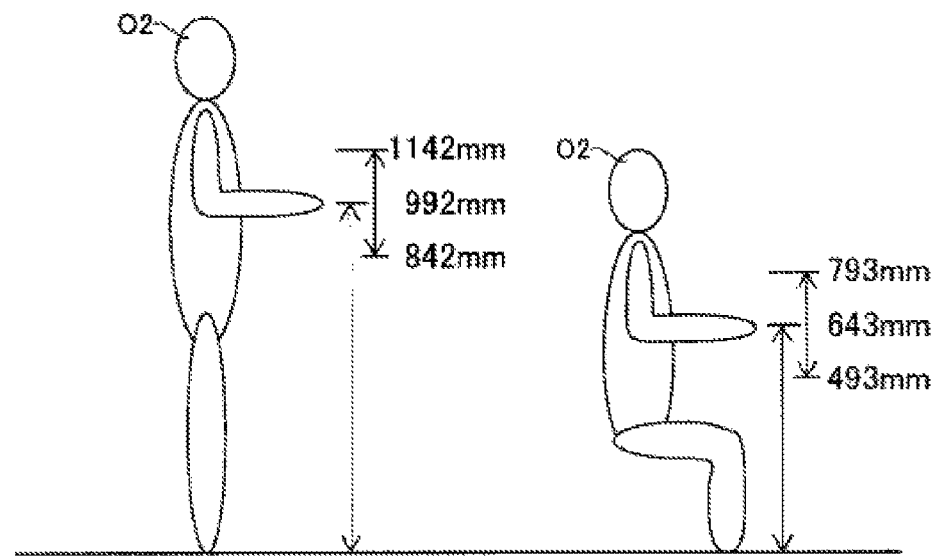

FIGS. 7A and 7B are views illustrating models of operators O, FIG. 7A illustrating a model of large operators O1, and FIG. 7B illustrating a model of small operators O2.

In FIG. 7A, the model of the large operators O1 is based on body data of German men. When the fifth largest model among 100 German male models selected at random stands and grips the operation handles 1 positioned at the neutral position A0 of the operation range A with his arms bent at right angles, the height position of the operation handles 1 is about 1176 mm, and the lower and upper limits of the height position of the operation range A are about 1026 mm and 1326 mm, respectively. On the other hand, when the fifth largest model sits down and grips the operation handles 1 positioned at the neutral position A0 of the operation range A with his arms bent at right angles, the height position of the operation handles 1 is about 703 mm, and the lower and upper limits of the height position of the operation range A are about 553 mm and about 853 mm, respectively.

In FIG. 7B, the model of the small operators O2 is based on body data of Japanese women. When the fifth smallest model among 100 Japanese female models selected at random stands and grips the operation handles 1 positioned at the neutral position A0 of the operation range A with her arms bent at right angles, the height position of the operation handles 1 is about 992 mm, and the lower and upper limits of the height position of the operation range A are about 842 mm and about 1142 mm, respectively. On the other hand, when the fifth smallest model sits down and grips the operation handles 1 positioned at the neutral position A0 of the operation range A with her arms bent at right angles, the height position of the operation handles 1 is about 643 mm, and the lower and upper limits of the height position of the operation range A are about 493 mm and about 793 mm, respectively.

Based on the aforementioned data, the height position of the operation handles 1 that allows plural operators O having different types of physique to take standing and sitting positions without any problem is as follows. First, the height position of the operation handles 1 positioned at the neutral position A0 of the operation range A in the standing position mode (the first mode) is preferably set to about 99 cm or more corresponding to the standing model of the small operators O2. This allows most operators O to comfortably operate the operation handles 1 while standing. When the operation handles 1 are configured to move down by 15 cm from the neutral position A0, the lower limit of the height position of the operation range A of the operation handles 1 in the standing position mode is 84 cm or more as described above.

The height position of the operation handles 1 positioned at the neutral position A0 in the standing position mode (the first mode) is preferably set to about 85 cm or more. When the operation handles 1 are configured to move down by 15 cm from the neutral position A0, the lower limit of the height position of the operation range A of the operation handles 1 in the standing position mode is higher than 70 cm, and the operation range A of the operation handles 1 is therefore within the clean area. Since the lower limit of the height position of the operation range A corresponding to the standing model of the small operators O2 is about 84 cm, setting the lower limit of the height position of the operation range A to 70 cm allows more operators O having different types of physiques to comfortably operate the operation handles 1 while standing up.

Next, the height position of the operation handles 1 positioned at the neutral position A0 of the operation range A in the sitting position mode (the second mode) is preferably set to about 64 cm or more corresponding to the sitting model of the small operators O2. This allows most operators O to comfortably operate the operation handles 1 while sitting down.

Next, the displacement (adjustment width) of the height position of the operation handles 1 at transition of the remote control apparatus 100 between the standing position mode and the sitting position mode is preferably set to about 35 cm or more. This is the difference between the height (about 99 cm) of the operation handles 1 positioned at the neutral position A0 corresponding to the standing model of the small operators O2 and the height (about 64 cm) of the operation handles 1 positioned at the neutral position A0 corresponding to the sitting model of the small operators O2.

In addition, the displacement of the height position of the operation handles 1 at transition of the remote control apparatus 100 between the standing position mode and the sitting position mode is preferably set to about 48 cm or more. This is the difference between the height (about 118 cm, the maximum height of the operation handles 1 positioned at the neutral position A0 in the standing position mode in this example) of the operation handles 1 positioned at the neutral position A0 corresponding to the standing model of the large operators O1 and the height (about 70 cm) of the operation handles 1 positioned at the neutral position A0 corresponding to the sitting model of the large operators O1.

As described above, the adjustment width of the height position of the operation handles 1 at transition between the standing position mode and the sitting position mode is greater than the adjustment width desirably set so as to fit to the different types of physique of the operators O in the standing position mode (about 19 cm as the difference between the height position of the operation handles 1 positioned at the neutral position A0, corresponding to the model of the large operators O1 and the height position of the operation handles 1 positioned at the neutral position A0, corresponding to the model of the small operators O2, for example) and the adjustment width desirably set so as to fit to the different types of physique of the operators O in the sitting position mode (about 6 cm as the difference between the height position of the operation handles 1 positioned at the neutral position A0 corresponding to the model of the large operators O1 and the height position of the operation handles 1 positioned at the neutral position A0 corresponding to the model of the small operators O2, for example).

If the positions of the operation handles 1 are set higher than about 118 cm (the height position of the operation handles 1 positioned at the neutral position A0 corresponding to the standing model of the large operators O1), the above-described adjustment width is further increased. It is then preferable that the adjustment width is 50 cm or more from the height position of the operation handles 1 in the standing position mode. Furthermore, the displacement of the height position of the operation handles 1 at transition of the remote control apparatus 100 between the standing position mode and the sitting position mode is preferably set to about 54 cm or more, which is the difference between the height (about 118 cm) of the operation handles 1 positioned at the neutral position A0 corresponding to the standing model of the large operators O1 and the height (about 64 cm) of the operation handles 1 positioned at the neutral position A0 corresponding to the sitting model of the small operators O2. As for definition of the operation range A, the design of the operation range A may be modified by considering the size of the operation handles 1 and the like. Although the vertical width of the operation range A is assumed to be 30 cm, the vertical width thereof may be set to 20, 25, or 35 cm, for example.

Second Embodiment

Next, a second embodiment is described with reference to FIG. 12. In the second embodiment, description is given of an example of the configuration of a remote control apparatus including plural display supporting arms, which is different from the first embodiment in which the remote control apparatus includes one display supporting arm.

As illustrated in FIG. 12, a remote control apparatus 400 according to a second embodiment includes plural display supporting arms 4. In the remote control apparatus 400, the display supporting arms 4 include display supporting arms 4a and 4b. In the example illustrated in FIG. 12, the scope type display 3a and non-scope type display 3b as the displays 3 are attached to the display supporting arms 4a and 4b of the remote control apparatus 400, respectively. The two displays 3 are placed right and left (side by side in the X direction). The display supporting arms 4a and 4b are examples of a first display supporting arm and a second display supporting arm, respectively.

In other words, the remote control apparatus 400 includes plural (two) mounting sections 41. Specifically, the remote control apparatus 400 includes the two display supporting arms 4 (4a, 4b). The mounting sections 41 are provided to the respective tips of the display supporting arms 4a and 4b. Both of the scope and non-scope type displays 3a and 3b can be thereby mounted on the remote control apparatus 400. This effectively increases the versatility of the displays 3.

In a second embodiment, the non-scope type display 3b, which is one of the displays 3, displays at least one of a previously acquired image of the surgical site, information indicating the state of the surgery, and operation information. The non-scope type display 3b displays X-ray images or magnetic resonance images previously captured. The other scope type or non-scope type displays a 3D or 2D image acquired from the endoscope 201b. This further increases the versatility and expandability such that, for example, the operator O performs surgery by mainly looking at the endoscopic image on the other display, while viewing, as needed, at least one kind of auxiliary information among the image of the surgery site previously acquired, the information indicating the state of the surgery, and the operation information.

The remote control apparatus 400 according to a second embodiment is configured so that the scope or non-scope type display 3a or 3b is selectively mounted as the main display 3. In addition, the non-scope type display 3b is mounted on the remote control apparatus 400 as an auxiliary display. The operator O can therefore select one of the immersive remote control apparatus and the open-type remote control apparatus and look at the auxiliary information during surgery. Since the remote control apparatus 400 is provided with plural mounting sections, it is possible to freely select on which side the main display is installed.

The display supporting arm 4a includes joints 43a, 43b, and 43c as the joints 43. The display supporting arm 4a includes a parallel link mechanism 44a as the parallel link mechanism 44. The joints 43a to 43c are respectively provided with electromagnetic brakes 431a, 431b, and 431c as electromagnetic brakes 431. The parallel link mechanism 44a is provided with an electromagnetic brake 441a as the electromagnetic brake 441. The joints 43a to 43c and parallel link mechanism 44a are examples of a joint and a first joint, respectively, and the electromagnetic brakes 431a to 431c and 441a are examples of a locking mechanism and a first locking mechanism, respectively.

The display supporting arm 4b includes joints 43d, 43e, and 43f as the joints 43. The display supporting arm 4b includes a parallel link mechanism 44b as the parallel link mechanism 44. The joints 43d to 43f are respectively provided with electromagnetic brakes 431d, 431e, and 431f as electromagnetic brakes 431 as illustrated in FIG. 3. The parallel link mechanism 44b is provided with an electromagnetic brake 441b as the electromagnetic brakes 441. The joints 43d to 43f and parallel link mechanism 44b are examples of a joint and a second joint, respectively, and the electromagnetic brakes 431d to 431f and 441b are examples of a locking mechanism and a second locking mechanism, respectively.

The trigger levers 321a are provided on the right and left sides of the scope type display 3a. The trigger levers 321b are provided on the right and left sides of the non-scope type display 3b. The trigger levers 321 are gripped together with respective grip sections 32 for unlocking operation. Specifically, the trigger levers 321a are configured to unlock the electromagnetic brakes 431a to 431c and 441a of the display supporting arm 4a. The trigger levers 321b are configured to unlock the electromagnetic brakes 431d to 431f of the display supporting arm 4b. The joints 43a to 43c and the parallel link mechanism 44a of the display supporting arm 4a and the joints 43d to 43f and the parallel link mechanism 44b of the display supporting arm 4b can be therefore unlocked independently of each other. The trigger levers 321a and 321b are examples of a first unlocking mechanism and a second unlocking mechanism.

In the example of FIG. 12, the scope type display 3a and non-scope type display 3b are attached to the two mounting sections 41. However, the scope type display 3a may be attached to each of the two mounting sections 41, or the non-scope type display 3b may be attached to each of the two mounting sections 41.

The other configurations of a second embodiment are the same as those of a first embodiment.

(Modification of Unlocking Mechanism)

In the examples illustrated in the above embodiments, the joints (the joints 43a to 43c and the parallel link mechanism 44) are unlocked by pressing both of the two trigger levers 321 on the right and left sides of the display 3. However, the way of unlocking the locking mechanisms of the joints is not limited to these examples.

For example, the unlocking mechanism may be configured so that all the joints are unlocked with only one of the two trigger levers 321 on the right and left sides of the display 3. In this case, the operator O is able to move the display 3 with one hand. The operator O therefore moves the display 3 more easily. The operator O is able to change the position of the display 3 with one hand regardless of whether the operator O is right-handed or left-handed.

Alternatively, the display 3 may be provided with only one trigger lever 321. Such a configuration includes fewer physical mechanisms around the display 3, reducing interferences with other portions. In this case, a display for left-handed operators or a display for right-handed operators may be provided as needed for use. When the remote control apparatus 100 includes a mounting section to which the display 3 is detachably attached, it is possible to select and use one from a display for right-handed operators and a display for left-handed operators as needed.

Moreover, the display 3 may be provided with three or more trigger levers 321. For example, two of the trigger levers 321 are provided on the right and left sides of the display 3 while one trigger lever 321 is provided as one of the foot pedals, and the display 3 is configured to move only when the three trigger levers 321 are pressed. In this case, the position of the display 3 cannot be changed until the operator O absolutely intends to move the position of the display 3.

When the display 3 is provided with plural trigger levers 321, each trigger lever 321 may be configured to unlock different joints. When the two trigger levers 321 are provided on the right and left of the display 3, for example, one of the right and left trigger levers 321 may be configured to unlock at least one (only the joint 43a, for example) of the joints contributing to horizontal movement of the display 3 while the other trigger lever 321 is configured to unlock at least one (the parallel link mechanism 44 in the example of FIG. 3) of the joints contributing to vertical movement of the display 3. In such a configuration, in addition to the aforementioned advantages of provision of plural trigger levers, movement of the display 3 may be limited so that the display 3 mainly moves in a desired direction. Such a configuration moreover allows only necessary joints to be movable, reducing burden on the display supporting arm 4 in the process of moving the display 3.

Figure 11:
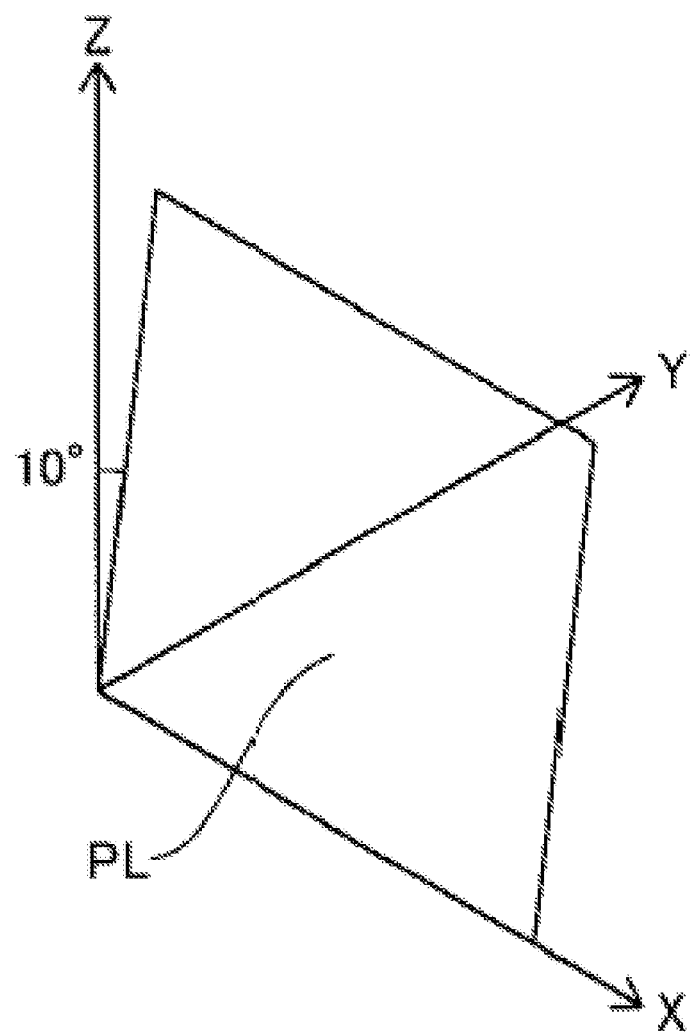
FIG. 11 is a perspective view illustrating a plane in a XYZ space by way of example.

When each joint of the display supporting arm 4 includes a motor and a position detector (an encoder, for example), the range of movement of the display 3 can be limited. For example, the display 3 is translated along a certain plane. When the display 3 is supported by the display supporting arm 4 with the display screen parallel to a plane PL tilted by 10 degrees to the XZ plane around the X axis in the XYZ coordinates as illustrated in FIG. 11, for example, the control apparatus 61 may perform a control so as to translate the display 3 along only the plane PL. The plane PL may be determined by the state of the angle adjustment joints 35, for example. The plane PL may be defined by the operation section 8b. To be specific, the angle of the plane PL along which the display 3 is translated may be inputted from the operation section 8b.

In order to change the position and angle of the display 3 more safely, the controller 61 may perform a control so that each joint is not unlocked while the operation handles 1 are being operated even if the pressing operation for the trigger levers 321 is detected. Whether the operation handles 1 are being operated can be detected with a motion sensor, for example. It is therefore possible to prohibit operating the operation handles 1 with one hand while operating the trigger lever 321 with the other hand, improving the safety as medical equipment.

It is preferable that the operation section 8b (see FIG. 4) is configured to set which to use among the above-described variations of the unlocking mechanism, that is, the condition to deactivate the locking mechanism of the joints by the trigger levers 321 as the unlocking mechanism. For example, the conditions are set as follows.

(1) Select one of the conditions: all the joints (the joints 43 and parallel link mechanism 44) are unlocked when all the plural trigger levers 321 are subjected to unlocking operation or when at least any one of the plural trigger levers 321 is subjected to unlocking operation.

(2) When the trigger levers 321 are provided on the right and left of the display 3 with space therebetween, set which to use among the trigger levers 321 for unlocking all the joints (for example, the right-handed or left-handed trigger lever)

(3) When the remote control apparatus includes plural trigger levers 321, set which joint to unlock by each trigger lever (4) Set the range where the display 3 is movable (movable along only the plane parallel to the inclination of the display 3, for example)

(5) When the remote control apparatus includes plural display supporting arms 4, select a display 3 to be moved

OTHER MODIFICATION

It should be understood that the disclosed embodiments are shown by way of example in every respect and are not limitative. The scope of the invention is not determined by the aforementioned embodiments but is specified by Claims. The scope of the invention includes all alternations (modifications) within meanings and scope equivalent to the scope of Claims.

The aforementioned first embodiment discloses an example(s) of the configuration in which one display supporting arm supporting the display is provided. The aforementioned second embodiment discloses an example(s) of the configuration in which two display supporting arms supporting the displays are provided. However, the invention is not limited to this example. For example, the remote control apparatus may be provided with three or more display supporting arms supporting displays, or the remote control apparatus may be provided with three or more displays.

The aforementioned first and second embodiments disclose examples of the configurations in which each display supporting arm includes plural joints. However, the invention is not limited to this example. For example, the display supporting arm may include only one joint.

The aforementioned first and second embodiments disclose examples of the configurations in which the displays are detachably attached to the display supporting arms. The invention is not limited to these examples. For example, the display may be fixed to the display supporting arm.

The aforementioned second embodiment disclose examples of the configurations in which the remote control apparatus is provided with the scope and non-scope type displays. However, the invention is not limited to these examples. For example, the remote control apparatus may be provided with only one scope type display or may be provided with only one non-scope type display.

The aforementioned first and second embodiments disclose examples of the configurations in which the mounted display is connected to the remote control apparatus with a cable so as to exchange information with the same. The invention is not limited to these examples. For example, the mounted display may be connected to the remote control apparatus through wireless communication so as to exchange information.

The aforementioned first and second embodiments disclose examples of the configuration in which the supporting mechanism moves the operation handles and armrest up and down. However, the invention is not limited to these examples. For example, the supporting mechanism may move the operation handles and armrest in the horizontal direction in addition to up and down movements.

The invention claimed is:

1. A remote control apparatus for a surgery assisting system including a manipulator that supports surgical equipment, comprising:
    a display configured to display an image captured by an endoscope and including a drip section that is provided on a lateral side of the display and that is to be gripped by an operator when moving the display;
    a display supporting arm that includes a plurality of links, a plurality of joints each of which connects adjacent two of the plurality of links, and a plurality of locking mechanisms provided to the plurality of joints respectively and configured to lock the plurality of joints respectively, wherein the display supporting arm supports the display;
    an operation handle that allows the operator to operate the manipulator; and
    an unlocking trigger configured, in response to an operation by the operator, to unlock the plurality of locked joints of the display supporting arm simultaneously, wherein the unlocking trigger is provided on the grip section of the display and unlocks the plurality of joints locked by the plurality of locking mechanisms only while being operated by the operator.

2. The remote control apparatus according to claim 1, wherein
the display supporting arm supports a back side of the display.

3. The remote control apparatus according to claim 1, wherein
the display is a scope type display or a non-scope type display.

4. The remote control apparatus according to claim 3, wherein
the scope type display includes a frame and a scope section supported by the frame,
the display supporting arm supports the frame, and
both lateral sides of the scope section are rotatably supported by the frame such that an angle of the scope section with respect to the frame is adjustable.

5. The remote control apparatus according to claim 1, wherein
each of the plurality of locking mechanisms comprises an electromagnetic brake.

6. The remote control apparatus according to claim 1, wherein
the unlocking trigger is configured to be pressed by gripping the grip section for unlocking the plurality of joints.

7. The remote control apparatus according to claim 1, further comprising:
a supporting section supporting the operation handle and the display supporting arm and movable up or down; and
a driving section including a motor and an encoder and configured to move the supporting section up or down to move the operation handle and the display.

8. The remote control apparatus according to claim 7, further comprising:
an armrest including an arm supporting section to support arms of the operator operating the operation handle, wherein
the supporting section supporting the armrest, and
the operation handle, the display and the armrest are moved up or down by moving the supporting section up or down by the driving section.

9. A remote control apparatus for a surgery assisting system including a manipulator that supports surgical equipment, comprising:
a scope type display configured to display an image captured by an endoscopy;
a display supporting arm that includes a joint and a locking mechanism configured to lock the joint and supports the scope type display;
an operation handle that allows an operator to operate the manipulator;
an unlocking mechanism configured, in response to an operation by the operator, to unlock the locked joint of the display supporting arm;
a non-scope type display;
a second display supporting arm that includes a joint and a locking mechanism configured to lock the joint and supports the non-scope type display; and
a second unlocking mechanism is configured, in response to an operation by the operator, to unlock the locked joint of the second display supporting arm.

10. A remote control apparatus for a surgery assisting system including a manipulator that supports surgical equipment, comprising:
a scope type display that includes a grip section provided on a lateral side of the scope type display and to be gripped by an operator and displays an image captured by an endoscope;
a display supporting arm that includes a plurality of links, a plurality of joints each of which connects adjacent two of the plurality of links, and a plurality of locking mechanisms provided to the plurality of joints respectively and configured to lock the plurality of joints respectively, wherein the display supporting arm supports the scope type display;
an operation handle that allows the operator to operate the manipulator; and
an unlocking trigger configured, upon being operated by the operator, to unlock the plurality of locked joints of the display supporting arm simultaneously, wherein
the unlocking trigger is provided to the grip section and unlocks the plurality of joints locked by the plurality of locking mechanisms only while being operated by the operator.

11. The remote control apparatus according to claim 10, wherein
the display supporting arm supports a back side of the display.

12. The remote control apparatus according to claim 10, wherein
the scope type display includes a frame and a scope section supported by the frame,
the display supporting arm supports the frame, and
both lateral sides of the scope section are rotatably supported by the frame such that an angle of the scope section with respect to the frame is adjustable.

13. The remote control apparatus according to claim 10, wherein
each of the plurality of locking mechanisms comprises an electromagnetic brake.

14. The remote control apparatus according to claim 10, wherein
the unlocking trigger is configured to be pressed by gripping the grip section for unlocking the plurality of joints.

15. The remote control apparatus according to claim 10, further comprising:
a supporting section supporting the operation handle and the display supporting arm and movable up or down; and
a driving section including a motor and an encoder and configured to move the supporting section up or down to move the operation handle and the display up or down.

16. The remote control apparatus according to claim 15, further comprising:
an armrest including an arm supporting section to support arms of the operator operating the operation handle, wherein
the supporting section supporting the armrest, and
the operation handle, the display and the armrest are moved up or down by moving the supporting section up or down by the driving section.

17. A remote control apparatus for a surgery assisting system including a manipulator that supports surgical equipment, comprising:
a display configured to display an image captured by an endoscope and including a first grip section provided on a first lateral side of the display and a second grip section provided on a second lateral side opposite to the first lateral side;

a display supporting arm that includes a plurality of links, a plurality of joints each of which connects adjacent two of the plurality of links, and a plurality of locking mechanisms provided to the plurality of joints respectively and configured to lock the plurality of joints respectively, wherein the display supporting arm supports the display;

an operation handle that allows an operator to operate the manipulator;

a first unlocking trigger provided on the first grip section of the display; and a second unlocking trigger provided on the second grip section of the display, wherein the first and second unlocking triggers are configured to unlock the plurality of locked joints of the display supporting arm simultaneously when the first and second unlocking triggers are operated simultaneously.

18. The remote control apparatus according to claim 17, wherein
each of the plurality of locking mechanisms comprises an electromagnetic brake.

19. The remote control apparatus according to claim 17, wherein
the first and second unlocking triggers are configured to unlock the plurality of joints locked by the plurality of locking mechanisms only while both of the first and second unlocking triggers are operated by the operator.

20. The remote control apparatus according to claim 17, wherein
the first unlocking trigger is configured to be pressed by gripping the first grip section and the second unlocking trigger is configured to be pressed by gripping the second grip section.

21. The remote control apparatus according to claim 17, further comprising:
a supporting section supporting the operation handle and the display supporting arm and movable up or down; and
a driving section including a motor and an encoder and configured to move the supporting section up or down to move the operation handle and the display.

22. The remote control apparatus according to claim 21, further comprising:
an armrest including an arm supporting section to support arms of the operator operating the operation handle, wherein
the supporting section supporting the armrest, and
the operation handle, the display and the armrest are moved up or down by moving the supporting section up or down by the driving section.

* * * * *